United States Patent [19]

Cregg

[11] Patent Number: 4,882,279
[45] Date of Patent: Nov. 21, 1989

[54] SITE SELECTIVE GENOMIC MODIFICATION OF YEAST OF THE GENUS PICHIA

[75] Inventor: James M. Cregg, San Diego, Calif.

[73] Assignee: Phillips Petroleum Company, Bartlesville, Okla.

[21] Appl. No.: 791,013

[22] Filed: Oct. 25, 1985

[51] Int. Cl.$^4$ .................. C12N 05/00; C12N 15/00; C12P 19/34

[52] U.S. Cl. .................. 435/172.3; 435/320; 435/68; 435/70; 435/91; 435/255; 435/232; 435/184; 435/272; 536/27; 935/19; 935/28; 935/37; 935/55; 935/56; 935/69

[58] Field of Search .............. 435/68, 70, 172.3, 91, 435/320, 255, 232, 189, 212; 536/27; 935/19, 28, 56, 69, 37, 55

[56] References Cited

U.S. PATENT DOCUMENTS

| 4,414,329 | 4/1983 | Wegner ........................... 435/255 |
| 4,518,698 | 5/1985 | Kikuchi et al. ................... 435/317 |
| 4,530,901 | 7/1985 | Weissmann ........................ 435/70 |

OTHER PUBLICATIONS

Scherer et al., Proc. Natl. Acad. Sci., vol. 76, (10), pp. 4951–4955, Oct. 1979, "Replacement of Chromosome Segments with Altered DNA Sequences Constructed in Vito".
Tolstorukov et al., Chem Abst., vol. 101(15), No. 126610w, 1984, "Genetic Mapping of the Yeast Pichia Pinus Part II, Mapping by Technical Analysis".
Proc. Natl. Acad. Sci. USA, vol. 78 (10), T. Orr-Weaver et al., pp. 6354–6358, (10/81).
Cell, vol. 33, J. Szostak et al., pp. 25–35, (5/83).
Gene, vol. 36, H. Rudolph et al., pp. 87–95, (1985).
Journal of Bacteriology, vol. 161, (1), H. Boucherie, pp. 385–392, (1/85).

Primary Examiner—Robin Teskin
Attorney, Agent, or Firm—J. E. Phillips

[57] ABSTRACT

Method for the site specific genomic modification of yeasts of the genus Pichia and novel DNA sequences useful therefor are provided. Pichia is transformed with a serially arranged linear DNA fragment comprising first and second insertable DNA fragments, which flank a marker gene. The insertable DNA sequences are homologous to defined portions of the Pichia genome and integrate by recombination at such defined sites. The resulting transformed organism contains the marker gene and any additional DNA sequences which are positioned between the insertable DNA fragments. In addition, the resulting transformed organism has either a disrupted or deleted sequence at the site of the genomic modification. Enhanced production of heterologous gene products is observed when using as the host for expression strains in which the alcohol oxidase gene has been disrupted. Upon disruption of the primary alcohol oxidase gene of Pichia, the existence of a second alcohol oxidase gene in Pichia was also discovered.

16 Claims, 18 Drawing Sheets

SITE SELECTIVE GENOMIC MODIFICATION OF YEAST OF THE GENUS PICHIA

This invention relates to the field of recombinant DNA technology. In one aspect, this invention relates to the integrative transformation of yeast. In another aspect, the present invention relates to site-directed mutation of yeast. In yet another aspect, the present invention relates to novel DNA sequences. In a further aspect, the present invention relates to novel organisms.

BACKGROUND

As recombinant DNA technology has developed in recent years, the controlled production by microorganisms of an enormous variety of useful polypeptides has become possible. Many eukaryotic polypeptides, such as for example, human growth hormone, leukocyte interferons, human insulin and human proinsulin have already been produced by various microorganisms. The continued application of techniques already in hand is expected in the future to permit production by microorganisms of a variety of other useful polypeptide products.

A basic element frequently employed in recombinant DNA technology is the plasmid, which is extrachromosomal, double-stranded DNA found in some microorganisms. Where plasmids have been found to naturally occur in microorganisms, they are often found to occur in multiple copies per cell. In addition to naturally occurring plasmids, a variety of man-made plasmids, or hybrid vectors, have been prepared. Unfortunately, it is not always possible for the host cell to maintain the plasmid. Instead, the plasmid is lost as the organism reproduces and passes through several generations of growth. Methods for the stable introduction of foreign DNA into suitable host organisms are therefore of great interest and potentially of great value.

Up to now, commercial efforts employing recombinant DNA technology for producing various polypeptides have centered on *Escherichia coli* as a host organism. However, in some situations *E. coli* may prove to be unsuitable as a host. For example, *E. coli* contains a number of toxic pyrogenic factors that must be eliminated from any polypeptide useful as a pharmaceutical product. The efficiency with which this purification can be achieved will, of course, vary with the particular polypeptide. In addition, the proteolytic activities of *E. coli* can seriously limit yields of some useful products. Furthermore, a number of heterologous gene products which have been produced in *E. coli* have been found to be produced in insoluble form. These and other considerations have led to increased interest in alternate hosts. In particular, the use of eukaryotic organisms for the production of polypeptide products is appealing.

The availability of means for the production of polypeptide products in eukaryotic systems, e.g., yeast, could provide significant advantages relative to the use of prokaryotic systems such as *E. coli* for the production of polypeptides encoded by recombinant DNA. Yeast has been employed in large scale fermentation for centuries, as compared to the relatively recent advent of large scale *E. coli* fermentations. Yeast can generally be grown to higher cell densities than bacteria and are readily adaptable to continuous fermentation processing. In fact, growth of yeast such as *Pichia pastoris* to ultra-high cell densities, i.e., cell densities in excess of 100 g/L, is disclosed by Wegner in U.S. Pat. No. 4,414,329 (assigned to Phillips Petroleum Co.). Additional advantages of yeast hosts include the fact that many critical functions of the organism, e.g., oxidative phosphorylation, are located within organelles, and hence are not exposed to possible deleterious effects caused by the organisms production of polypeptides foreign to the wild-type host cells. As a eukaryotic organism, yeast may prove capable of glycosylating expressed polypeptide products, which may prove of value where such glycosylation is important to the bioactivity of the polypeptide product. It is also possible that as a eukaryotic organism, yeast will exhibit the same codon preferences as higher organisms, thus tending toward more efficient production of expression products from mammalian genes or from complementary DNA (cDNA) obtained by reverse transcription from, for example, mammalian mRNA.

The development of poorly characterized yeast species as host/vector systems is severely hampered by the lack of knowledge about transformation conditions and suitable means for stably introducing foreign DNA into the host cell. In addition, auxotrophic mutants are often not available, precluding a direct selection for transformants by auxotrophic complementation. If recombinant DNA technology is to fully sustain its promise, new host/vector systems must be devised which facilitate the manipulation of DNA as well as optimize the expression of inserted DNA sequences so that the desired polypeptide products can be prepared under controlled conditions and in high yield.

OBJECTS OF THE INVENTION

An object of the invention, therefore, is a process for inserting DNA into the genome of yeast at preselected locations of the yeast genome.

Another object of the invention is a process for preparing stable auxotrophic mutants of yeast which are essentially incapable of reversion.

Yet another object of the invention is stable auxotrophic mutants which are essentially incapable of reversion.

Still another object of the invention is novel DNA sequences useful for the transformation of yeast.

A further object of the present invention is the production of an alcohol oxidase mimus mutant host for the enhanced production of heterologous proteins by yeast.

These and other objects of the invention will become apparent from the disclosure and claims herein provided.

STATEMENT OF THE INVENTION

In accordance with the present invention, there has been developed a novel process for the site directed modification of the genome of yeast of the genus Pichia. By tranforming yeast with a linear DNA fragment comprising, at each end, insertable DNA sequences, i.e., sequences with homology to the host genome, each being at least about 200 nucleotides in length, and at least one additional DNA fragment, e.g., a selectable marker gene, thereinbetween, the marker gene and the flanking insertable DNA sequences are taken up by the host in high frequency. As a result of transformation with this linear DNA, modified yeast strains are produced wherein the DNA sequence at the site of integration has been disrupted and/or deleted, and the selectable marker gene, as well as any other DNA included as part of the transforming linear DNA fragment, have been incorporated into the genome of the host yeast.

Foreign DNA inserted into the genome of the host yeast in the above described manner is stably maintained through many generations of growth by the host. The practice of the present invention thereby eliminates the problem of loss of foreign DNA due to plasmid instability when foreign DNA is instead provided as part of an autonomously-replicating extrachromosomal fragment or when foreign DNA is instead integrated into the genome as part of a circular DNA molecule. Such circular DNA molecule integrations result in the insertion of foreign DNA sequences flanked by a direct repeat of host genomic sequences into the host genome. Since such direct repeat sequences are substrates for further recombination, foreign DNA inserted between the direct repeat sequences are unstable.

The site-directed genomic modification of the present invention makes possible the production of mutants lacking all or selected portions of specific genes. By eliminating substantial portions of the gene in which a mutation is desired, the likelihood of reversion of the mutation is essentially eliminated. The resulting mutant strains produced in accordance with the invention are thus very stable mutants.

The site-directed genomic modification of the present invention, together with in vitro recombinant DNA techniques known by those of skill in the art, also makes possible a wide variety of precise host genomic modifications, e.g., the addition of one or more heterologous genes to the host genome, the alteration of regulatory sequences which control the expression of a native gene, the replacement of a native gene with a gene of non-native origin, and the like.

It has surprisingly been found that the methanol induced expression of heterologous genes in Pichia is dramatically enhanced by employing as the host for gene expression a strain of Pichia in which the primary alcohol oxidase gene of Pichia has been disrupted.

It has further been found that strains of the organism *Pichia pastoris* have a second, alcohol oxidase gene which allows a host strain in which the primary alcohol oxidase gene has been disrupted to retain the ability to grow on methanol, albeit at a reduced rate relative to native *Pichia pastoris*.

BRIEF DESCRIPTION OF THE FIGURES

FIG. 4 is a restriction map of plasmid pYMI3a.

FIG. 14 is a restriction map of plasmid pYMI12a.

FIG. 16c shows the known alcohol oxidase (AOX) encoding portion of the AOX1 gene locus (with reference to FIG. 16a).

Figure 1:
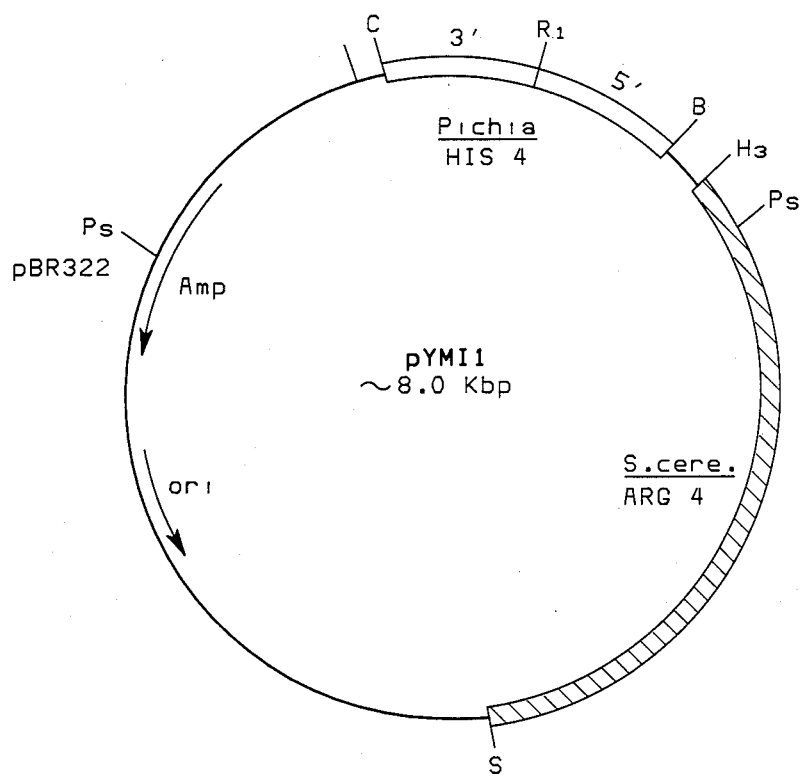
FIG. 1 is a restriction map of plasmid pYMI1.

The following abbreviations are used throughout this specification to represent the restriction enzymes employed:

| Abbreviation | Restriction Enzyme |
|---|---|
| As | AsuII |
| B | BamHI |
| $B_2$ | BglII |
| C | ClaI |
| $R_1$ | EcoRI |
| $R_5$ | EcoRV |
| $H_3$ | HindIII |
| $Hp_1$ | HpaI |
| Kp | KpnI |
| Nr | NruI |
| Ps | PstI |
| $Pv_2$ | PvuII |
| Rs | RsaI |
| S | SalI |
| $S_3$ | Sau3II |
| Sm | SmaI |
| Sp | SphI |
| St | StuI |
| Th | ThaI |
| Xb | XbaI |
| Xh | XhoI |

In the attached figures, restriction sites employed for the manipulation of DNA fragments, but which are destroyed upon ligation, are indicated by enclosing the abbreviation for the destroyed site in parenthesis.

DETAILED DESCRIPTION OF THE INVENTION

In accordance with the present invention, there is provided a process for the site-selective genomic modification of yeasts of the genus Pichia at a predetermined genomic site which comprises transforming a host strain of the genus Pichia with a serially arranged linear DNA fragment comprising a first insertable DNA fragment, a selectable marker gene, and a second insertable DNA fragment. The first and second insertable DNA fragments are each at least about 200 nucleotides in length and have nucleotide sequences which are homologous with separate portions of the native Pichia genome at the site at which the genomic modification is to occur. The selectable marker gene is a gene whose product confers a selectable phenotype upon cells which receive the gene, e.g., an antibiotic resistance gene or a biosynthetic gene which allows the cell to synthesize a nutrient required for growth. The selectable marker gene, when present on a DNA vector, allows only those cells which receive the vector DNA to grow under selective growth conditions. It is essential that the selectable marker gene be positioned between the first and second insertable DNA fragments, and that the insertable DNA fragments be positioned in the same orientation with respect to each other as they exist in the genome of the host cell undergoing genomic modification by the linear DNA fragment.

Further in accordance with the present invention, there is provided a serially arranged linear DNA fragment which comprises a first insertable DNA fragment, a selectable marker gene and a second insertable DNA fragment. The first and second insertable DNA fragments are each at least about 200 nucleotides in length, have nucleotide sequences which are homologous with portions of the genomic DNA of species of the genus Pichia, and are oriented with respect to one another in the linear fragment as they exist in the genome of Pichia. The marker gene is positioned between the first and second insertable DNA fragments.

The basic element with which species of the genus Pichia are transformed in accordance with the present invention contains a minimum of three components:

a first insertable DNA fragment,
a second insertable DNA fragment, and
a selectable marker gene.

The first and second insertable DNA fragments should each be at least about 200 nucleotides in length, with lengths generally in the range of about 200 up to 5,000 nucleotides commonly being employed. Preferably, for ease of manipulation and handling, fragments in the range of about 500 to 2000 nucleotides are employed.

Nucleotide sequences useful as the first and second insertable DNA fragments are nucleotide sequences which are homologous with separate portions of the native Pichia genomic site at which genomic modification is to occur. Thus, for example, if genomic modification is to occur at the locus of the alcohol oxidase gene, the first and second insertable DNA fragments employed will be sequences homologous with separate portions of the alcohol oxidase gene locus. For genomic modification in accordance with the present invention to occur, the two insertable DNA fragments must be oriented with respect to one another in the linear fragment in the same relative orientation as they exist in the Pichia genome.

The three minimum components of the transforming DNA employed in the practice of the present invention are serially arranged to form a linear DNA fragment wherein the selectable marker gene is positioned between the first insertable fragment and the second insertable fragment. Exemplary selectable marker genes include, but are not limited to, the ARG4 gene from *Pichia pastoris* and *Saccharomyces cerevisiae*, the HIS4 gene from *Pichia pastoris* and *S. cerevisiae*, the G418 phosphotransferase gene from the *E. coli* transposable element Tn601, and the like. Those of skill in the art also recognize that numerous suitable flanking sequences, i.e., the first and second insertable DNA fragments, can be derived from genes which have been isolated from the *Pichia pastoris* genome. Exemplary genes include, but are not limited to the alcohol oxidase genes (AOX1 and AOX2; Pichia has two alcohol oxidase genes), the dihydroxyacetone synthase gene (DAS), the argininosuccinate lyase gene (ARG4), the histidinol dehydrogenase gene (HIS4), and the like.

The transforming linear DNA fragments can include a variety of other DNA sequences, such as for example, heterologous genes, i.e., any gene or portion of a gene not normally found at that locus of the genome where insertion in the host cell is to occur, expression of which is desired in *P. pastoris*. Generally, the term heterologous refers to DNA not native to the host Pichia cell. The heterologous gene can optionally be combined with a regulatory region which will independently control the production of the heterologous gene product, or the heterologous gene can be expressed in the transformed cell under the influence of the native regulatory region of the gene which has been disrupted in the transformation process.

In addition, the transforming linear DNA fragment employed in the practice of the present invention can also include bacterial plasmid DNA, such as for example, pBR322 or pBR325 sequences. Such bacterial sequences are useful for the in vitro manipulation and production by amplification in *E. coli* of these DNA sequences.

An especially useful form for the transforming, linear DNA is as a closed circular plasmid comprising:

a first insertable DNA fragment,
a second insertable DNA fragment,
a selectable marker gene, and
bacterial plasmid DNA.

This plasmid can also contain additional DNA sequences as described hereinabove.

In a preferred embodiment, the closed circular plasmid is constructed composed of two portions, the "transforming" portion and the "bacterial" portion. The transforming portion comprises, serially arranged, the first insertable DNA fragment, the selectable marker gene, and the second insertable DNA fragment, wherein the first and second insertable DNA fragments are oriented with respect to one another as they exist in the Pichia genome, with the selectable marker gene positioned between the first insertable DNA fragment and the second insertable DNA fragment. The bacterial portion is then positioned so as to connect the first insertable DNA fragment and the second insertable DNA fragment, thereby forming a closed, circular vector.

The closed, circular vector prepared as described in the previous paragraph can be employed to produce large quantities of plasmid in *E. coli*, which plasmid is then isolated, and digested with appropriate restriction enzymes to cleave the transforming portion from the bacterial portion. The linear, transforming portion of yeast DNA can then be employed to transform strains of the genus Pichia in order to effect the desired genomic modification.

Of course, it is recognized by those of skill in the art that the "transforming" portion of the closed circular plasmid described above can contain additional DNA sequences. For example, the bacterial sequences employed in vitro for manipulation and production of the DNA by amplification in *E. coli* can be part of the transforming DNA, i.e., the bacterial sequences can, like the selectable marker gene sequences, also be positioned between the first insertable DNA fragment and the second DNA fragment. When such a configuration of DNA components is employed, the bacterial sequences would also be incorporated into the genome of the host yeast which is subjected to the process for genomic modification of the present invention.

The transformation of *Pichia pastoris* has been previously described in copending application Ser. No. 666,579 of Stroman et al., assigned to Phillips Petroleum Company. The experimental procedures employed for the transformation of *Pichia pastoris* are presented in greater detail below (see Example I). Yeast strains of the genus Pichia can be transformed by enzymatic digestion of the cell walls to give spheroplasts; the spheroplasts are then mixed with the transforming DNA and incubated in the presence of calcium ions and polyethylene glycol, then regenerated in selective growth medium. The transforming DNA includes a selectable marker gene, which allows selection for cells which have taken up transforming DNA, since only transformed cells are capable of survival and growth under the selective growth conditions employed (the selective growth conditions are a function of the selectable marker gene employed as part of the transforming DNA).

When strains of Pichia in which the primary alcohol oxidase gene (AOX1) was disrupted were employed as hosts for the expression of heterologous genes, it was surprisingly observed that the level of expression of the heterologous gene products, when under the control of some promoters (e.g., AOX1 or DAS promoters), was increased several-fold relative to the level of expression obtained when a fully alcohol oxidase-competent host was employed. As a result of this observation and further exploration of this phenomenon, it has been determined that a general method to increase the expression level in host organisms of heterologous genes exists, which comprises growing the host strain under nutritionally limiting conditions on a substrate for which a strong substrate-responsive promoter region exists, wherein the heterologous gene is under the regulatory control of this strong, substrate-responsive promoter.

The "nutritionally limiting conditions" required for the increased gene expression of the present invention can be provided either by feeding the cells limiting amounts of a nutrient or by employing a mutant host which, as a result of the mutation, is nutritionally limited under certain growth conditions. Thus, for example, when it is desired to enhance the level of expression of heterologous genes maintained under the control of the strong alcohol oxidase or dihydroxyacetone synthase promoters, both of which promoters are responsive to the presence of methanol in the growth media, either the use of a host which is partially defective in its ability to utilize methanol, or the use of methanol-limited growth conditions with a fully alcohol oxidase competent host, will provide the required nutritionally limiting conditions so that enhanced gene expression will be achieved.

It is believed that the method for enhancing the expression of heterologous gene products described herein is a general method useful in any organism for which promoters which respond to nutritional limitations exist. Thus, by placing a heterologous gene under the control of such a promoter region, then culturing the host organism under conditions of nutritional limitation with respect to the nutrient(s) which cause the strong promoter to be turned on, increased gene expression should occur. The presently preferred means to provide nutritionally limited growth conditions is to employ a mutant host organism which is partially defective in the ability to metabolize the nutrient(s) which causes some promoters to be expressed at much higher levels than in the non-mutant host. In Pichia, this has been demonstrated as described in greater detail in Example V.

When a strain of *Pichia pastoris* in which the primary alcohol oxidase gene was disrupted by the inventive method for genomic modification was cultured with methanol as carbon source, it was surprisingly found that such strains defective in the primary alcohol oxidase gene were still able to grow on methanol albeit at a reduced rate relative to wild type Pichia cells. This observation indicated the possible presence of a second alcohol oxidase gene in methanol utilizing strains of Pichia.

Screening of a library of Pichia chromosomal DNA has led to the isolation of a 3 kbp fragment, which appears to encode a portion of a second alcohol oxidase gene (AOX2). The fragment has been deposited as an insert into pBR322 (at the unique BamHI site). The plasmid is referred to as pPG3.0, and is carried by the *E. coli* host LE392. This strain has been deposited with the Northern Regional Research Center of the United States Department of Agriculture in Peoria, Ill. to insure access to the public upon issuance of this application as a patent and has been assigned the assession number NRRL B-18022.

Figure 16:
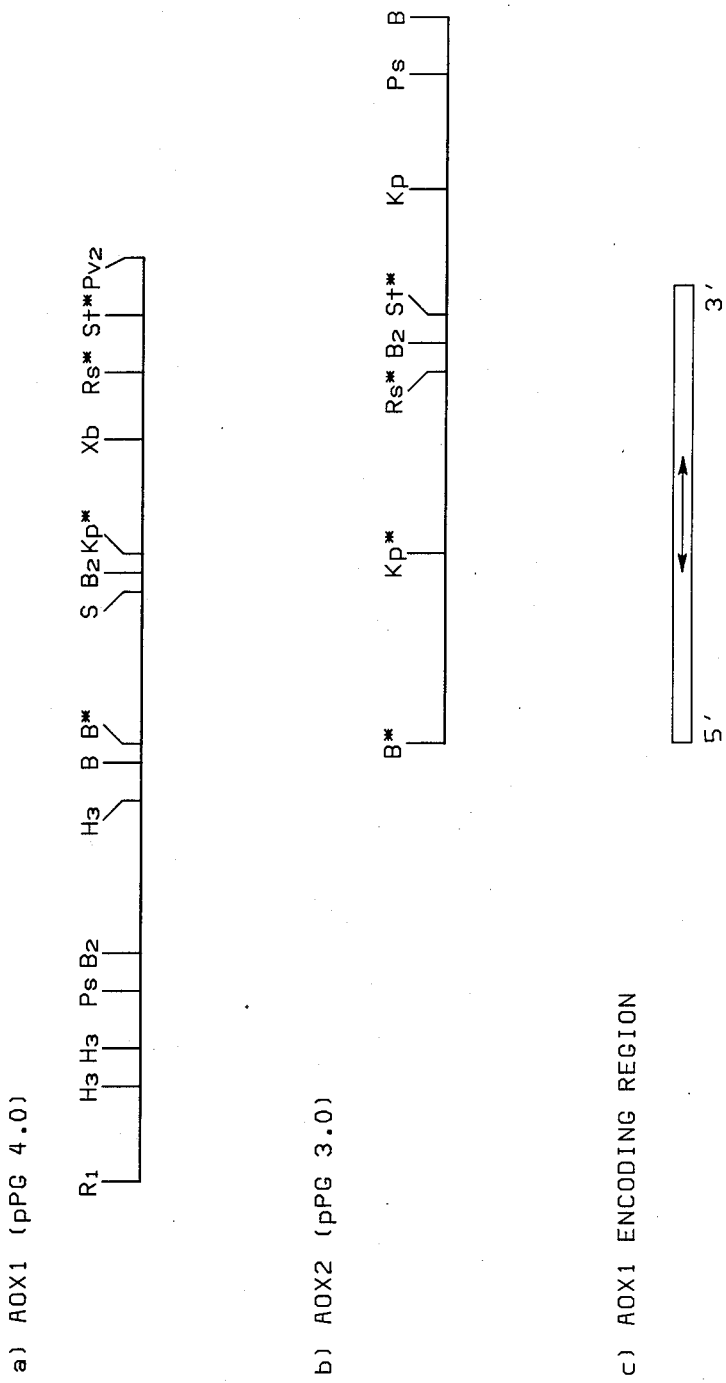
FIG. 16 is a restriction map of the Pichia inserts in the pBR322-based plasmids pPG4.0 and pPG3.0. The insert shown in FIG. 16a is from the locus of the first Pichia alchol oxidase gene (AOX1), while the insert shown in FIG. 16b is from the locus of the second Pichia alcohol oxidase gene (AOX2).

A restriction map of pPG3.0 is set in FIG. 16b, where it is compared with a genomic fragment of the primary alcohol oxidase gene, pPG4.0. The latter fragment has been previously disclosed and described in detail in copending application Ser. No. 666,391 of Stroman et al., assigned to Phillips Petroleum Company. A comparison of the two alcohol oxidase genes (see FIG. 16) makes it clear that the two fragments are not merely overlapping portions of the same genomic locus. There is clearly some homology between the two fragments, as evidenced by the existence of several common restriction sites on the two fragments. The restriction sites common to the two genes, AOX1 and AOX2, are denoted in FIG. 16 by asterisks. However, the existence of several restriction sites on each fragment which are not present on the other indicate that there are several differences in the fragments at the nucleotide level.

The invention will now be described in greater detail by reference to the following non-limiting examples.

EXAMPLES

The buffers and solutions employed in the following examples have the compositions given below:

1M Tris buffer
121.1 g Tris base in 800 mL of $H_2O$;
adjust pH to the desired value by adding concentrated (35%) aqueous HCl;
allow solution to cool to room temperature before final pH adjustment;
dilute to a final volume of 1 L.

TE buffer
1.0 mM EDTA in 0.01M (pH 7.4) Tris buffer

LB (Luria-Bertani)
5 g Bacto-tryptone
Medium
5 g Bacto-yeast extract
2.5 g NaCl
in 1 L of water, adjusted to pH 7.5 with NaOH 2B Medium
0.2% $NH_4PO_4$
1.2% $Na_2HPO_4$
0.013% $MgSO_4.7H_2O$
0.074% $CaCl_2.2H_2O$
2 μg/mL biotin
1 μg/mL thiamine
100 μg/mL tryptophan
0.4% dextrose
0.2% casamino acids YPD Medium 1% Bacto-yeast extract
2% Bacto-peptone
2% Dextrose
SD Medium
6.75 g yeast nitrogen base without amino acids (DIFCO)
2% Dextrose in 1 L of water
SED
1M Sorbitol
25 mM EDTA
50 mM DTT
SCE Buffer
9.1 g Sorbitol
1.47 g Sodium citrate
0.168 g EDTA
50 mL H$_2$O
—pH to 5.8 with HCl
CaS
1M Sorbitol
10 mM CaCl$_2$
—filter sterilize
PEG Solution
20% polyethylene glycol-3350
10 mM CaCl$_2$
10 mM Tris-HCl (pH 7.4)
—filter sterilize
SOS
1M Sorbitol
0.3x YPD medium
10 mM CaCl$_2$ The following abbreviations are used throughout the examples with the following meaning:
EDTA ethylenediamine tetraacetic acid
SDS sodium dodecyl sulfate
DTT dithiothreitol

EXAMPLE I

*Pichia pastoris* Transformation Procedure

A. Cell Growth

1. Inoculate a colony of *Pichia pastoris* GS115 (NRRL Y-15851) into about 10 mL of YPD medium and shake culture at 30° C. for 12-20 hrs.
2. After about 12-20 hrs., dilute cells to an OD$_{600}$ of about 0.01-0.1 and maintain cells in log growth phase in YPD medium at 30° C. for about 6-8 hrs.
3. After about 6-8 hrs, inoculate 100 mL of YPD medium with 0.5 mL of the seed culture at an OD$_{600}$ of about 0.1 (or equivalent amount). Shake at 30° C. for about 12-20 hrs.
4. Harvest culture when OD$_{600}$ is about 0.2-0.3 (after approximately 16-20 hrs) by centrifugation at 1500 g for 5 minutes.

B. Preparation of Spheroplasts

1. Wash cells once in 10 mL of sterile water. (All centrifugations for steps 1-5 are at 1500 g for 5 minutes.)
2. Wash cells once in 10 mL of freshly prepared SED.
3. Wash cells twice in 10 mL of sterile 1M Sorbitol.
4. Resuspend cells in 10 mL SCE buffer.
5. Add 5-10 μL of 4 mg/mL Zymolyase 60,000 (Miles Laboratories). Incubate cells at 30° C. for about 30-60 minutes.

Since the preparation of spheroplasts is a critical step in the transformation procedure, one should monitor spheroplast formation as follows: add 100 μL aliquots of cells to 900 μL of 5% SDS and 900 μL of 1M Sorbitol before or just after the addition of zymolyase and at various times during the incubation period. Stop the incubation at the point where cells lyse in SDS but not in sorbitol (usually between 30 and 60 minutes of incubation).

6. Wash spheroplasts twice in 10 mL of sterile 1M Sorbitol by centrifugation at 1000 g for 5-10 minutes. (The time and speed for centrifugation may vary; centrifuge enough to pellet spheroplasts but not so much that they rupture from the force.)
7. Wash cells once in 10 mL of sterile CaS.
8. Resuspend cells in total of 0.6 mL of CaS.

C. Transformation

1. Add DNA Samples (up to 20 μL volume) to 12×75 mm sterile polypropylene tubes. (DNA should be in water or TE buffer; for maximum transformation frequencies with small amounts of DNA, it is advisable to add about 1 μL of 5 mg/mL sonicated *E. coli* DNA to each sample.)
2. Add 100 μL of spheroplasts to each DNA sample and incubate at room temperature for about 20 minutes.
3. Add 1 mL of PEG solution to each sample and incubate at room temperature for about 15 minutes.
4. Centrifuge samples at 1000 g for 5-10 minutes and decant PEG solution.
5. Resuspend samples in 150 μL of SOS and incubate for 30 minutes at room temperature.
6. Add 850 μL of sterile 1M Sorbitol and plate aliquots of samples as described below.

D. Regeneration of Spheroplasts

1. Recipe for Regeneration Agar Medium:
 a. Agar-KCl- 9 g Bacto-agar, 13.4 g KCl, 240 mL H$_2$O, autoclave.
 b. 10× Glucose- 20 g Dextrose, 100 mL H$_2$O, autoclave.
 c. 10× SC- 6.75 g Yeast Nitrogen Base without amino acids, 100 mL H$_2$O, autoclave. (Add any desired amino acid or nucleic acid up to a concentration of 200 μg/mL before or after autoclaving.)
 d. Add 30 mL of 10× Glucose and 30 mL of 10× SC to 240 mL of the melted Agar-KCl solution. Add 0.6 mL of 0.2 mg/mL biotin and any other desired amino acid or nucleic acid to a concentration of 20 μg/mL. Hold melted Regeneration Agar at 55°-60° C.

2. Plating of Transformation Samples:
Pour bottom agar layer of 10 mL Regeneration Agar per plate at least 30 minutes before transformation samples are ready. Distribute 10 mL aliquots of Regeneration Agar to tubes in a 45°-50° C. bath during the period that transformation samples are in SOS. Add aliquots of transformation samples described above to tubes with Regeneration Agar and pour onto bottom agar layers of plates.

3. Determination of Quality of Spheroplast Preparation:
Remove 10 μL of one sample and dilute 100 times by addition to 990 μL of 1M Sorbitol. Remove 10 μL of the 100 fold dilution and dilute an additional 100 times by addition to a second 990 μL aliquot of 1M Sorbitol. Spread 100 μL of both dilutions on agar plates containing YPD medium to determine the concentration of unspheroplasted whole cells remaining in the preparation. Add 100 μL of each dilution to 10 mL of Regeneration Agar supplemented with 40 μg/mL histidine to determine total regeneratable spheroplasts. Good values for a transformation experiment are 1-3×10$^7$ total

EXAMPLE II

Site-specific Insertion of the Saccharomyces ARG4 Gene and pBR322 and Deletion of the Pichia HIS4 in GS190 (NRRL Y-18014)

Figure 2:
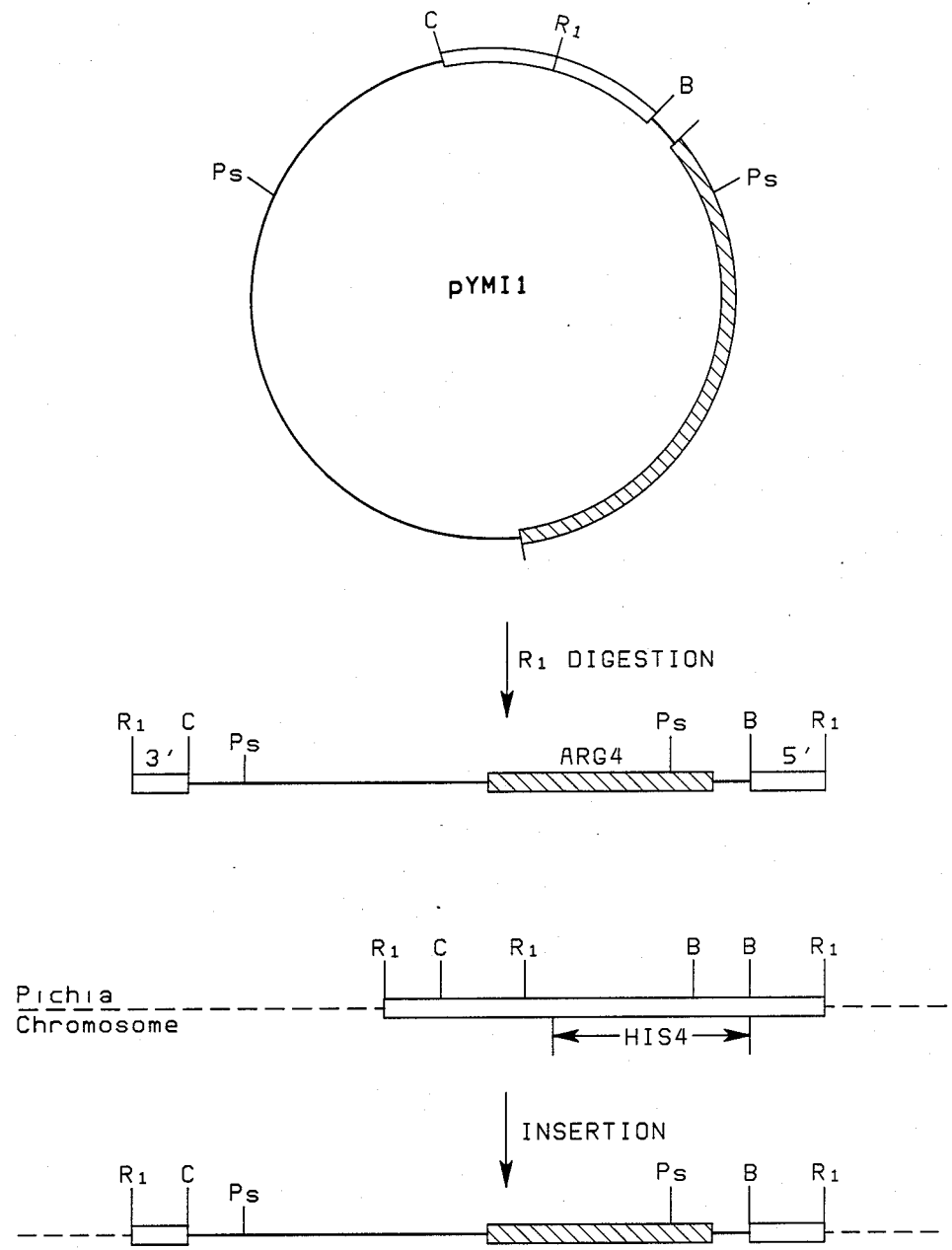
FIG. 2 illustrates the insertion of a portion of plasmid pYMI1 into the HIS4 locus of the Pichia chromosome.

FIG. 1 shows plasmid pYMI1 and FIG. 2 shows a diagram of events which result in the plasmid's site-directed insertion into the *P. pastoris* genome. The vector is designed to insert the Saccharomyces ARG4 gene and DNA sequences from pBR322 into the *Pichia HIS4* locus, simultaneously deleting the entire HIS4 gene locus from the Pichia genome. Other sequences, such as expression cassettes, could easily be inserted into pYMI1 and then similarly incorporated into the *P. pastoris* genome.

Figure 3:
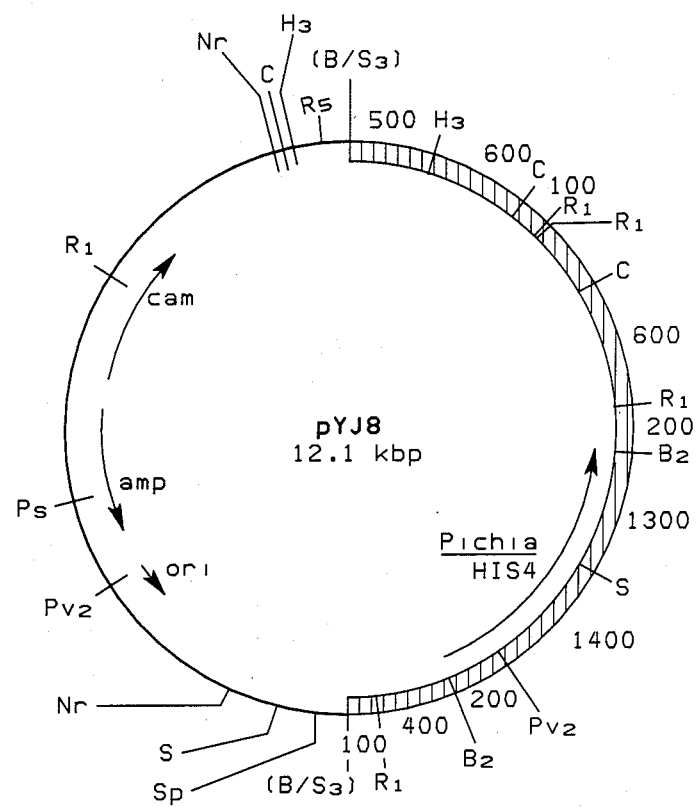
FIG. 3 is a restriction map of plasmid pYJ8.
Figure 17:
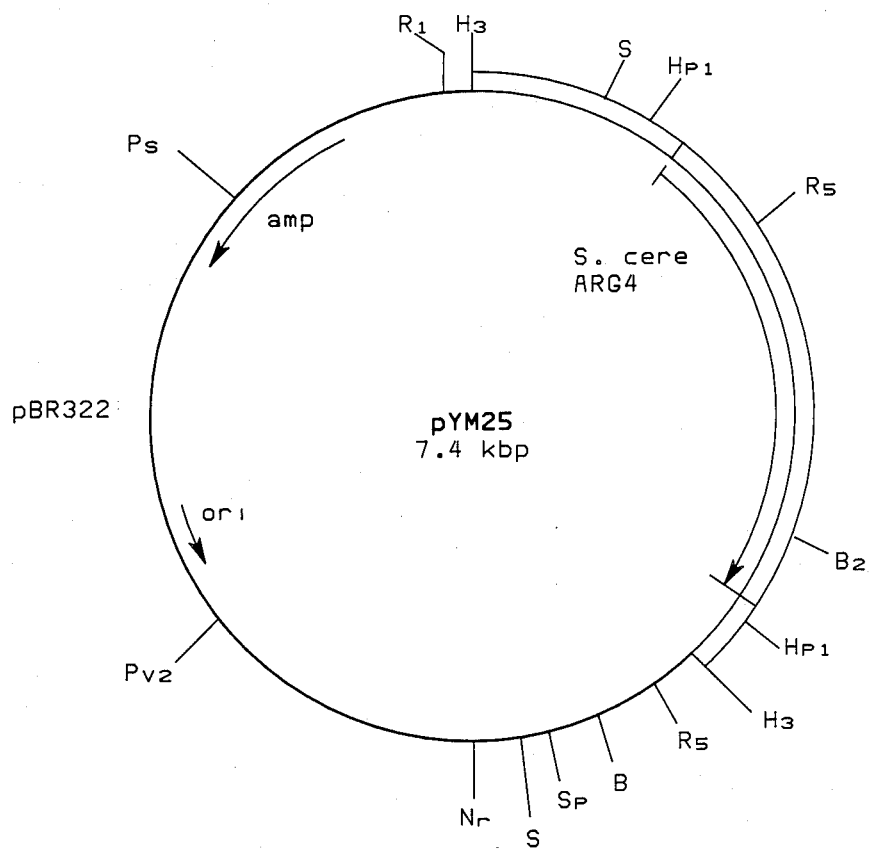
FIG. 17 is a restriction map of plasmid pYM25.

Plasmid pYMI1 is composed of an EcoRI-BamHI fragment which is located, in situ, at the 5' end of the Pichia HIS4 gene, and an EcoRI-ClaI fragment which is located 3' of the Pichia HIS4 gene. Both HIS4 gene-flanking fragments can be obtained from plasmid pYJ8 (available in an *E. coli* host from the Northern Regional Research Center of the United States Department of Agriculture in Peoria, Ill., as NRRL B-15889; see FIG. 3), and are about 400 bp long and joined at their EcoRI termini in pYMI1. As a selectable marker, the pYMI1 vector contains a 2.6 kbp HindIII-SalI fragment from pYM25 (available in an *E. coli* host as NRRL B-18015; see FIG. 17) which encodes the Saccharomyces arginosuccinate lyase (the ARG4 gene product). When cut with EcoRI, pYMI1 becomes linear, with the HIS4 gene-flanking fragments at its termini.

The *P. pastoris* arg4 strains, GS190 (NRRL Y-18014), was transformed with EcoRI-cut pYMI1 to arginine prototrophy (Arg+). The regeneration agar medium was supplemented with 40 µg/mL of histidine to avoid exerting selection pressure against transformants which required histidine as a result of the HIS4 gene deletion.

The Arg+ transformants were then screened for those which had become His− as a result of deletion of the HIS4 gene. To screen for His− transformants, the regeneration agar with the embedded Arg+ colonies was transferred to a sterile 50 mL tube which contained 25 mL of sterile water. The agar was then pulverized by mixing with a Brinkman Instruments Polytron homogenizer at setting 5 for about 1 minute. The yeast cells were separated from the agar by filtration through three layers of sterile gauze. A portion of the yeast cells was then sonicated, diluted and spread on SD medium agar plates supplemented with 40 µg/mL of histidine.

For sonication, samples of cells were diluted to an $A_{600}=0.1$ and sonicated for 10 seconds with a Sonifier Cell Disrupter 350 (Branson Sonic Power Co.) at power setting 4, a treatment which is sufficient to separate cells but not to reduce cell viability. After 2-3 days, colonies which grew on the SD plus histidine agar plates were replica plated to sets of SD plates, one with and one without histidine.

The proportion of Arg+ His− colonies averaged 0.7% of the total Arg+ transformants. Genomic DNA from three Arg+ His− strains was examined by Southern blot hybridization. The entire HIS4 gene was absent in all three and the linear plasmid was inserted as shown at the bottom of FIG. 2.

Besides the fact that the GS190-pYMI1 strain requires histidine and no longer requires arginine for growth, no other changes in nutritional requirements or growth rates were observed.

EXAMPLE III

Deletion of the HIS4 Gene from *P. pastoris* NRRL Y-11430

Figure 4:
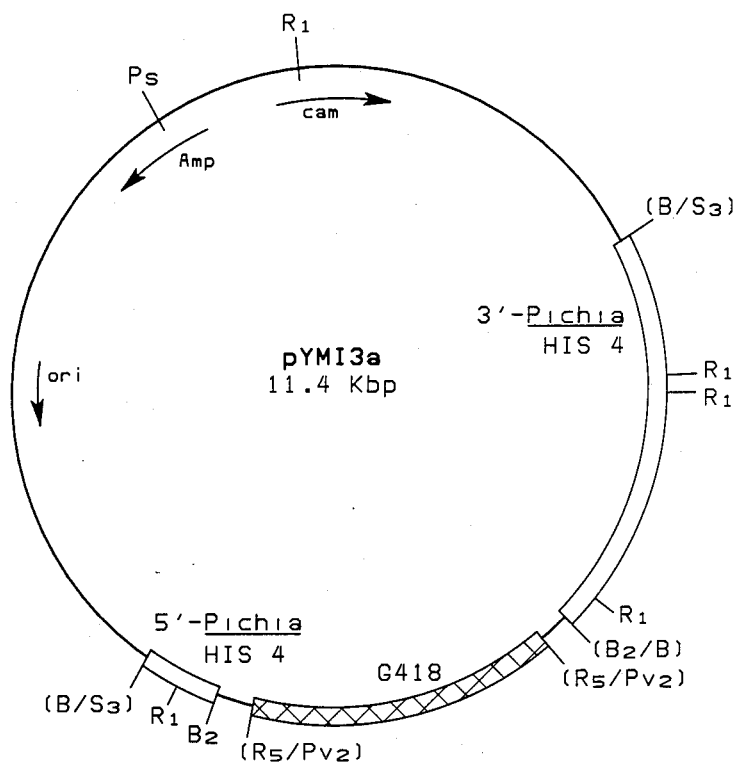
Figure 5:
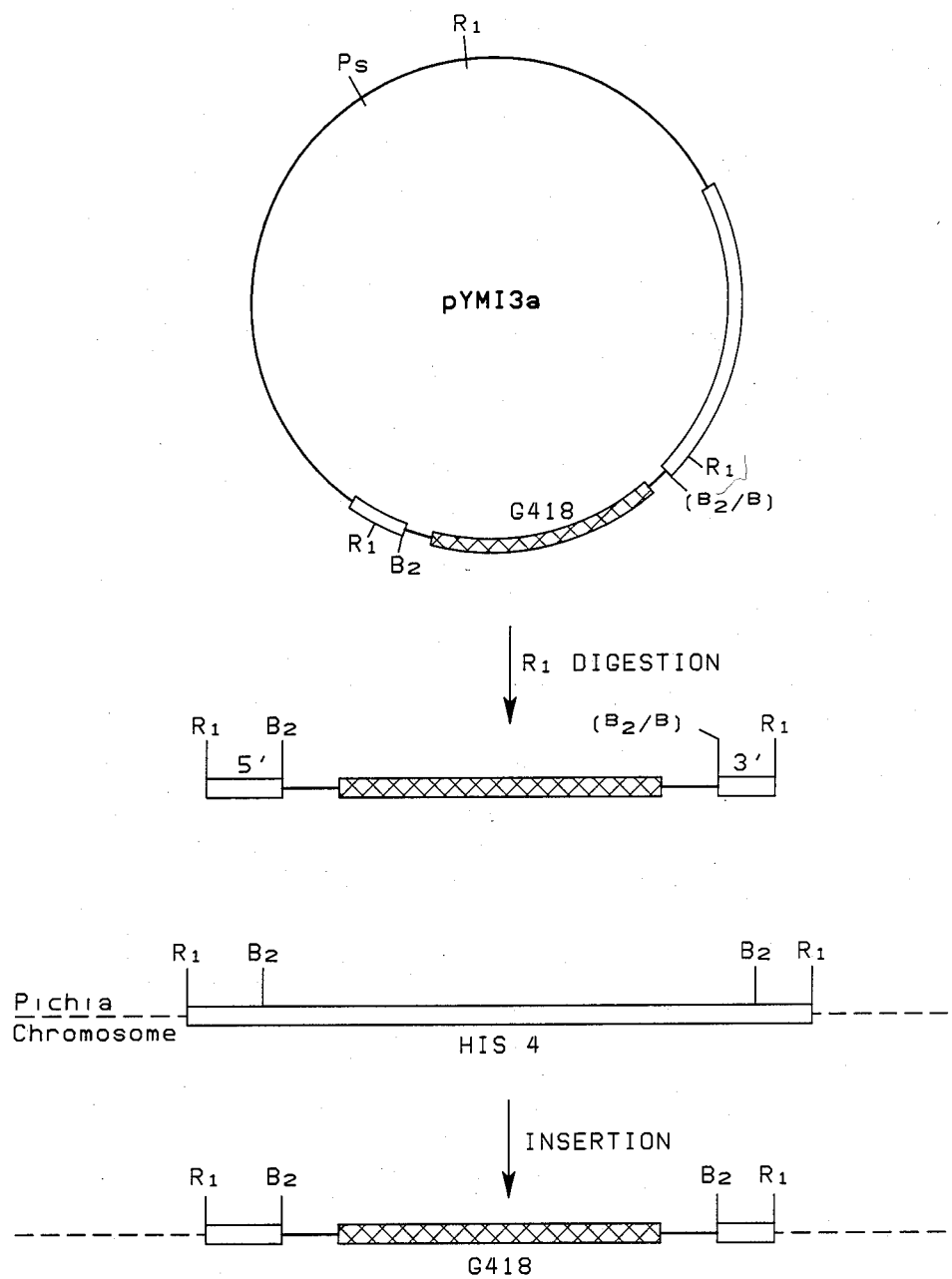
FIG. 5 illustrates the insertion of a portion of plasmid pYMI3a into the HIS4 locus of the Pichia chromosome.
Figure 6:
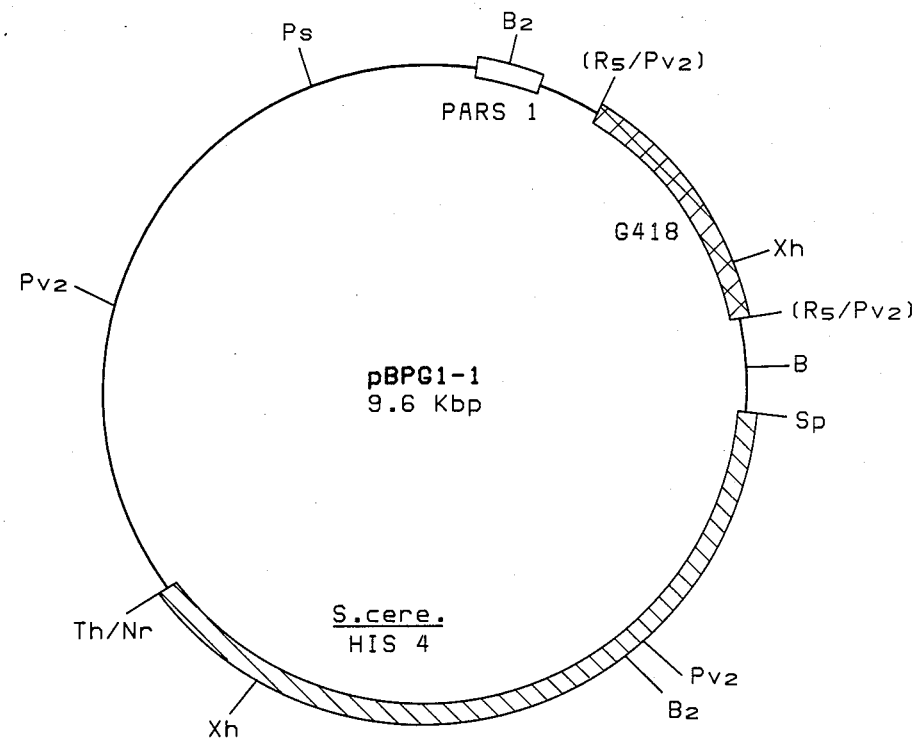
FIG. 6 is a restriction map of plasmid pBPG1-1.

FIG. 4 shows plasmid pYMI3a and FIG. 5 sets forth the events which result in the linear insertion of a fragment from the plasmid into the HIS4 locus of *P. pastoris* strain NRRL Y-11430. The vector contains the G418 resistance gene (G418$^R$) from pBPG1-1 (available from the United States Department of Agriculture, Northern Regional Research Center in Peoria, Ill., in an *E. coli* host as strain NRRL B-18020; see FIG. 6) as the selectable marker. The G418$^R$ gene was moved from pBPG1-1 on an approximately 2.2 kbp BamHI (pBR322 site)/BglII (PARS1 site) fragment and inserted into the BalII site of pYJ8 (NRRL B-15889; see FIG. 3), replacing the 2.7 kbp BglII fragment which contains the Pichia HIS4 gene.

The vector pYMI3a was digested with EcoRI to produce a 2.9 kbp fragment which contained the G418$^R$ gene flanked by about 450 and 250 bp of DNA from the region located just 5' and 3' of the HIS4 gene, respectively. The EcoRI cut plasmid was transformed into the *P. pastoris* host.

Transformants were selected by their ability to grow in the presence of 300 µg/mL of the antibiotic, G418. For the G418 selection, the regeneration medium agar was modified from that described in Example I, part D as follows:

1. Recipe for regeneration agar medium:
   a. Agar-sorbitol- 9 g bacto-agar, 54.6 g Sorbitol, 240 mL H$_2$O, autoclave.
   b. 10× glucose- 20 g Dextrose, 100 mL H$_2$O, autoclave.
   c. 10× YP- 10 g yeast extract, 20 g peptone, 100 mL H$_2$O, autoclave.
   d. Add 30 mL of 10× glucose and 30 mL of 10× YP to 240 mL of melted agar-sorbitol solution. Hold melted regeneration medium agar at 55° C.–60° C.

2. Plating of transformants. Sample:

At least 30 minutes before transformation samples were ready, 10 mL/plate bottom agar layer of regeneration medium agar supplemented with 600 µg/mL of G418 was poured. During the period the transformation samples were in SOS, 10 mL aliquots of regeneration medium agar (without G418) were distributed to tubes in a 45°–50° C. bath. When transformation samples were ready, aliquots of the samples were added to the tubes with the regeneration agar and poured onto the 10 mL bottom agar layer containing G418. Plates were incubated at 30° C. for 3–5 days.

After colonies had formed on the regeneration agar plates with G418, the cells were screened for their ability to grow without histidine. Cells were extracted from the regeneration agar, sonicated, and spread on SD medium agar plates supplemented with 40 µg/mL of histidine as described in Example II. After 2-3 days incubation at 30° C., the colonies were replica plated onto SD medium agar plates with and without histidine.

Approximately 0.1% of the G418$^R$ colonies were His− (2 out of approximately 2,000 screened). Southern blot hybridization experiments showed that the HIS4 gene was deleted from the genomes of both His− strains and that both genomes contained the G418$^R$ gene as shown in FIG. 5. One of these His− strains, given the laboratory designation KM31 (available from the United Stated Department of Agriculture, Northern Regional Research Center in Peoria, Ill., as NRRL Y-18018) has been successfully transformed with several HIS4-containing Pichia-based plasmids such as, for example, pSAOH5 (available in an *E. coli* host as NRRL B-15862), which provides further evidence that KM31 is specifically a HIS4 gene deletion organism.

This is the first time that "wild type" *P. pastoris* NRRL Y-11430 has been transformed directly (i.e., without first isolating and characterizing an auxotrophic derivative). A possible advantage of these HIS4 mutant strains is that since they were constructed by the site-specific insertion/deletion method, they are free of secondary mutations which probably exist in Pichia auxotrophic hosts which are produced, for example, by chemical mutagenesis, such as for example GS115 (NRRL Y-15851) and GS190 (NRRL Y-18014).

Note that deletion of the Pichia HIS4 gene from the Pichia genome by insertion of the EcoRI fragment from pYMI3a did not result in the addition of large portions of pBR322 (as occured when pYMI1 was inserted; see Example II). Since most autonomous ARS-based Pichia expression vectors, such as, for example pSAOH5 (see FIG. 9) are primarily composed of sequences from pBR322 and the Pichia HIS4 gene, these autonomous vectors have little homology with the genome of these Pichia HIS4 deletion hosts, and, therefore, should not frequently integrate.

EXAMPLE IV

Disruption of the Primary Alcohol Oxidase Gene

Pichia strains lacking the alcohol oxidase genes (the primary alcohol oxidase gene is referred to herein as AOX1 and the secondary alcohol oxidase gene is referred to herein as AOX2) are of interest for at least two reasons. First, as an aid in the studies on regulation of gene expression by methanol. For example, with a mutant strain defective in the AOX1 and AOX2 genes, as described in greater detail in Example VII, evidence can be obtained as to whether methanol or some other metabolite (formaldehyde, formate, etc.) is the actual inducing molecule of methanol regulated genes. A second interest in an AOX-defective Pichia strain lies in the possibility that such a strain might express higher levels of heterologous gene products as described in greater detail in Examples V and VI.

Figure 7:
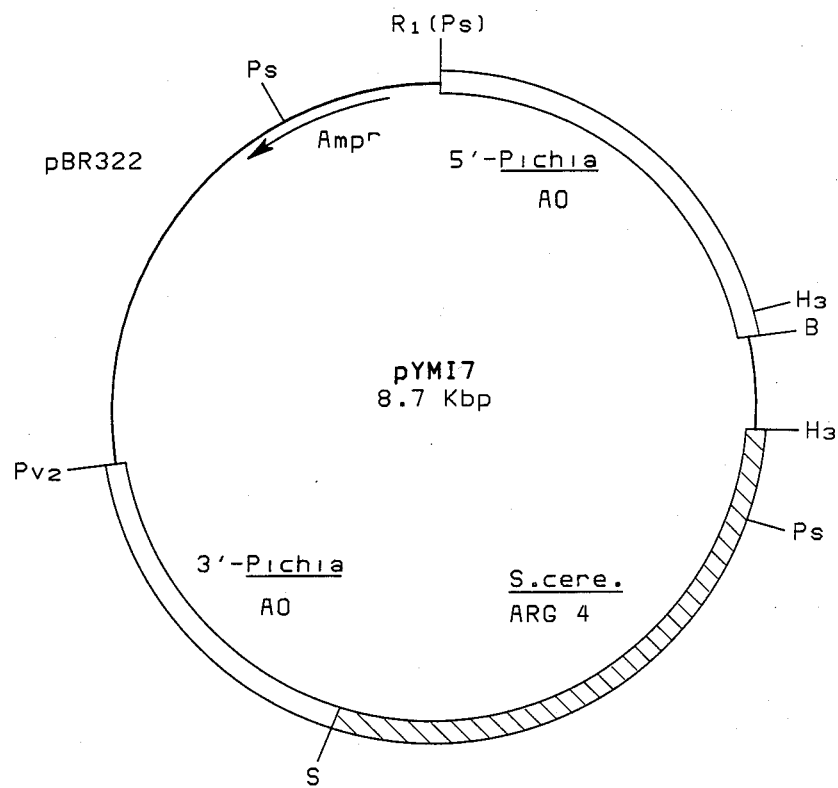
FIG. 7 is a restriction map of plasmid pYMI7.
Figure 8:
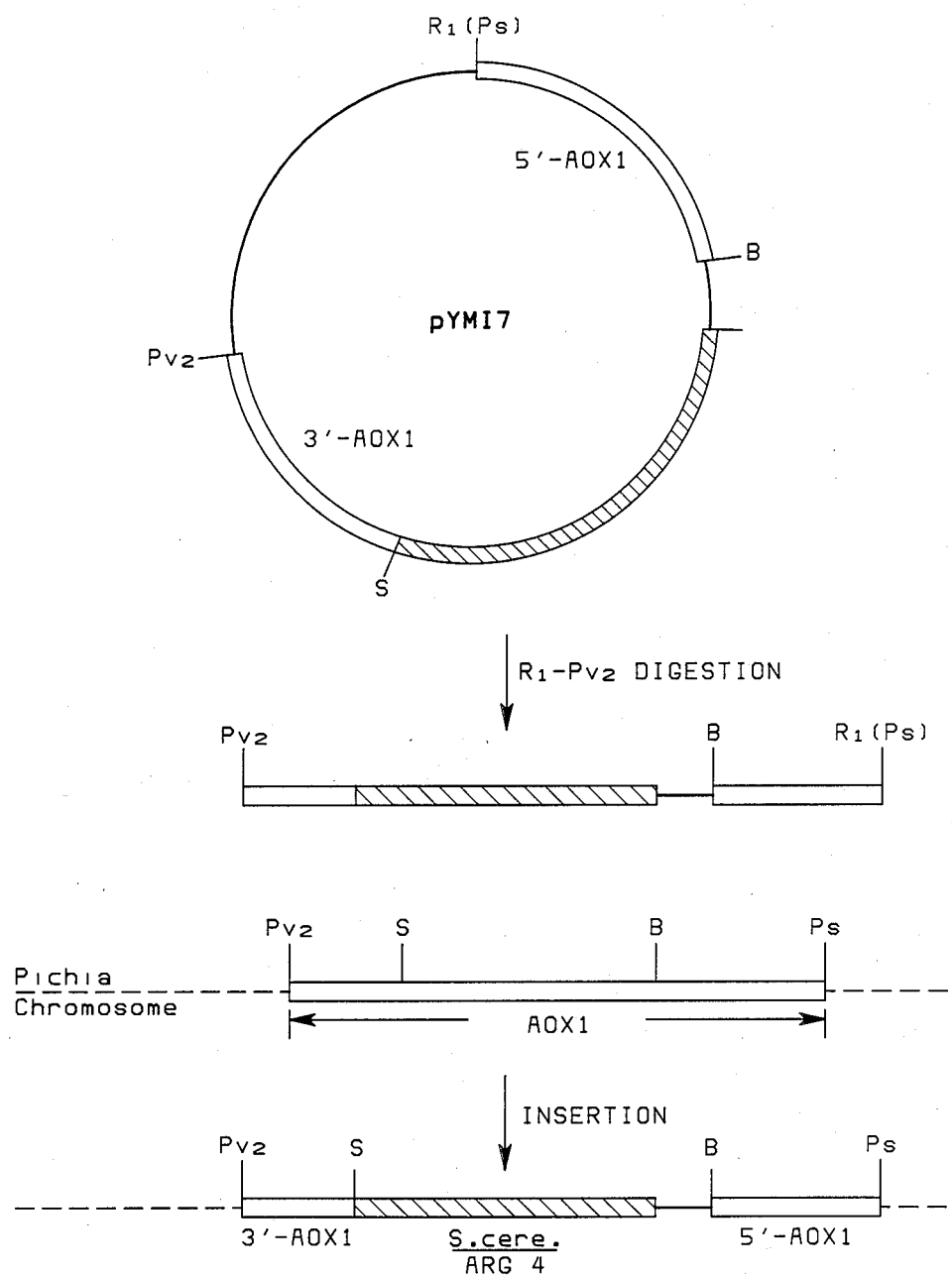
FIG. 8 illustrates the insertion of a portion of plasmid pYMI7 into the alcohol oxidase locus of the Pichia chromosome.

To disrupte the AO gene, plasmid pYMI7 was created (FIG. 7). The plasmid was constructed by inserting a 2.9 kbp BamHI-SalI fragment from plasmid pYM25 (NRRL B-18015; see FIG. 17) which contains the Saccharomyces ARG4 gene into BamHI-cut pPG4.0 (NRRL B-15868; see FIG. 16a for a restriction map of the Pichia portion of this plasmid). The insertion results in a deletion of about 600 bp from the 5'-portion of the AOX1 gene (about one fourth of the gene). Plasmid pYMI7 was linearized by digestion with PvuII and EcoRI and transformed into PPF1 (arg4 his4, NRRL Y-18017) by selecting for Arg+ prototrophs. Transformants were extracted from the regeneratioon agar and sonicated as described in Example II and spread on SD medium agar plates containing 0.1% glucose (instead of 2%) and 40 μg/mL histidine. Colonies which resulted were then replica plated onto a set of SD medium agar plates (containing histidine) with the following carbon sources: (1) no carbon; (2) 0.5% methanol; and (3) 2% glucose. About 81.0% of the Arg+ colonies could not grow normally on methanol. Southern blot analysis of genomic DNA from two of these methanol nonutilizers, i.e., KM71 and KM72, confirmed that the AOX1 gene was disrupted in these strains, and that the vector was inserted as shown at the bottom of FIG. 8.

The PPF1-pYM17 alcohol oxidase defective constructions having the genotype: (his4 aox1:Sarg4) are of great potential value. For example, since the strain is his4, Pichia vectors which contain the HIS4 gene as a selectable marker, such as, for example, pSAOH5 (NRRL B-15862; see FIG. 9), can be transformed into this host, as described more fully in Example V, below.

EXAMPLE V

Methanol-Regulated Expression of the lacZ gene in an Alcohol Oxidase-Defective Mutant Strain of *Pichia pastoris*

This example describes experiments on the expression of the lacZ gene in the Pichia host KM71 (a PPF1-pYM17 alcohol oxidase defective construction) which was prepared as described in Example IV.

Figure 18:
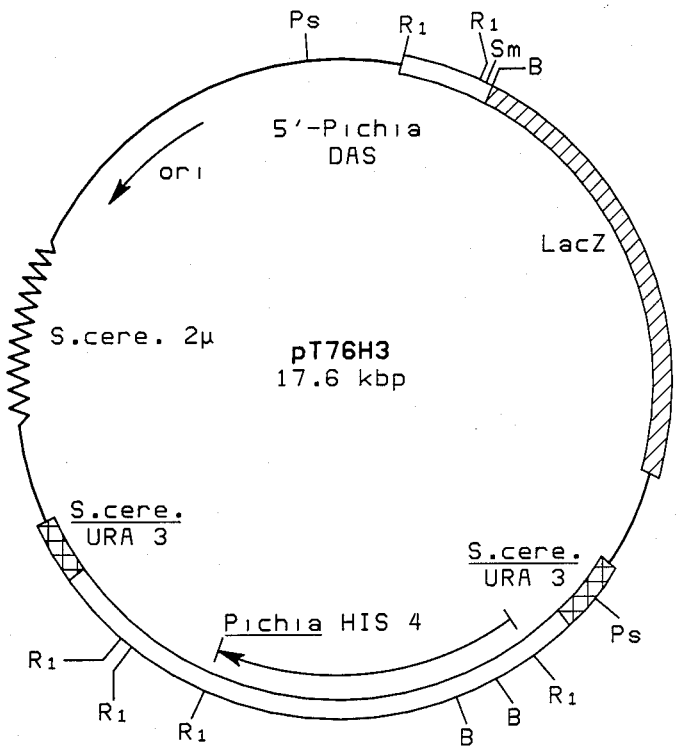
FIG. 18 is a restriction map of plasmid pT76H3.

The Aox1− host for these comparative experiments was KM71 (his4 aox1::SARG4) and the Aox1+ host was PPF1 (arg4 his4; NRRL Y-18017). The AOX1 promoter-lacZ expression cassette transformed into both strains was on the plasmid pSAOH5 (see FIG. 9, NRRL B-15862). Several stable His+ transformants from both strains were isolated. Their genomic DNAs were examined by Southern blot analysis to obtain a matched set of strains, each containing pSAOH5 integrated at the AOX1 promoter locus. Similarly, the dihydroxyacetone synthase (DAS) promoter-lacZ gene fusion was transformed into KM71 and PPF1 on plasmid pT76H3 (see FIG. 18; NRRL B-18000) by selecting for histidine prototrophy.

Each of the four strains was initially grown in SD medium except with 2% glycerol as sole carbon and energy source instead of 2% glucose. Each culture was then shifted, i.e., collected by centrifugation and transferred to a different medium, i.e., SD medium with 0.5% methanol as sole carbon source. Samples of these cultures were assayed for β-galactosidase, with the results summarized in Table I.

TABLE I

| | β-Galactosidase, units/μg* | | | |
|---|---|---|---|---|
| | Aox1+ host | | Aox1− host | |
| | Promoter → | | | |
| Time, hrs | AOX1 | DAS | AOX1 | DAS |
| 0 | 0 | 0 | 0 | 0 |
| 2 | 3 | 2 | 5 | 4 |
| 4 | 11 | 8 | 7 | 7 |
| 10 | 18 | 9 | 12 | 11 |
| 16 | 17 | — | 26 | — |
| 20 | 21 | 12 | 38 | 18 |
| 25 | — | 16 | — | 24 |
| 30 | 18 | — | 43 | 27 |
| 32 | — | 22 | — | 37 |
| 42 | 14 | — | 72 | — |
| 50 | — | 22 | — | 48 |
| 54 | 14 | — | 48 | — |

*β-Galactosidase Assay

A. Solutions required:

| 1. Z-buffer: | | Final concentration |
|---|---|---|
| $Na_2HPO_4 \cdot 7H_2O$ | 16.1 g | 0.06 M |
| $NaH_2PO_4$ | 5.5 g | 0.4 M |
| KCl | 0.75 g | 0.01 M |

-continued

| 1. Z-buffer: | | Final concentration |
|---|---|---|
| MgSO$^4$.7H$^2$O | 0.246 g | 0.001 M |
| 2-mercaptoethanol | 2.7 mL | 0.05 M |
| fill up to 1L; pH should be 7 | | |

2. O-Nitrophenyl-β-D-galactoside (ONPG)

Dissolve 400 mg ONPG (Sigma N-1127) in 100 mL of distilled water to make a 4 mg/mL ONPG solution.

B. Assay Procedure:

1. Withdraw an aliquot from the culture medium (20–50 OD$_{600}$ of yeast cells), centrifuge and wash cell pellet with cold sterile water.

2. Add 100 µL of Z buffer to the cell pellet and 0.2 µg of acid washed 0.45–0.50 mm glass beads. Hold all samples on ice. Vortex the mixture at the highest setting four (4) times for one minute each time. Samples should be held on ice for at least one minute between vortexings.

3. Transfer lysates to microcentrifuge tubes and centrifuge in a microfuge at 4° C. for 5 minutes. Transfer the supernatants to fresh microcentrifuge tubes and hold the extracts on ice.

4. The concentration of total protein in an extract was estimated using the Bio-Rad Laboratories (Bradford) protein assay method. For this the Bio-Rad Dye Reagent Concentrate was diluted with four volumes of deionized H$_2$O and filtered through Whatman 3MM paper. A standard concentration curve was then prepared by adding 3, 10, 30, and 100 µg of bovine serum albumen (BSA) in 100 µL Z buffer to a set of 13×100 mm glass tubes each of which contained 2.5 mL of the dye reagent. The samples were mixed and held at room temperature for 5 minutes and their optical densities at 595 nm determined. For the extracts, 3, 10, and 30 µL samples were brought to 100µL with a solution containing the Z buffer and assayed for protein content as described above. A protein concentration value for each extract was then interpolated using the BSA concentration curve.

5. For the β-galactosidase assays, 10 µL of a 10× dilution of extract was added to 1 mL of Z buffer and the mixture was incubated for 5 minutes at 30° C.

6. Start reaction by adding 0.2 mL of ONPG (4 mg/ml), vortex.

7. Stop reaction by adding 0.5 ml of a 1M Na$_2$CO$_3$ solution at appropriate time points (usually between 1 and 30 minutes, and at A$_{420}$ <1).

8. Read absorbance of supernatant at 420 nm.

C. Calculation of β-galactosidase Activity Units:

1 U=1 nmole of orthonitrophenol (ONP) formed per minute at 30° C. and a pH 7.

1 nmole of ONP has an absorbance at 420 nm (A$_{420}$) of 0.0045 with a 1 cm pathlength; thus, an absorbance of 1 at 420 nm represents 222 nmole ONP/mL, or 378 nmole/1.7 mL since the total volume of supernatant being analyzed is 1.7 mL. Hence, Units expressed in the Tables are calculated:

$$U = \frac{A^{420}}{t(min)} \times 378$$

Each of the four cultures showed almost no detectable β-galactosidase activity during the glycerol-growth phase. About 10–20 hours after shifting to methanol medium, the two cultures which contained the AOX1-lacZ and DAS-lacZ expression cassettes in the Aox1$^+$ host showed β-galactosidase activity leveling off at about 20 units of β-galactosidase activity per µg of protein. However, the AOX1-lacZ cassette in the Aox1$^-$ background showed activity reaching around 60 units/µg. The DAS-lacZ cassette in the Aox1$^-$ host showed an increase in β-galactosidase activity levels as well. Thus, the transformed Aox1$^-$ host, expressed β-galactosidase at 2–3 times the level of the transformed isogenic-Aox1$^+$ strain, PPF1.

EXAMPLE VI

Insertion of the Hepatitis B Surface Antigen Gene and Deletion of the AOX1 Gene

Figure 9:
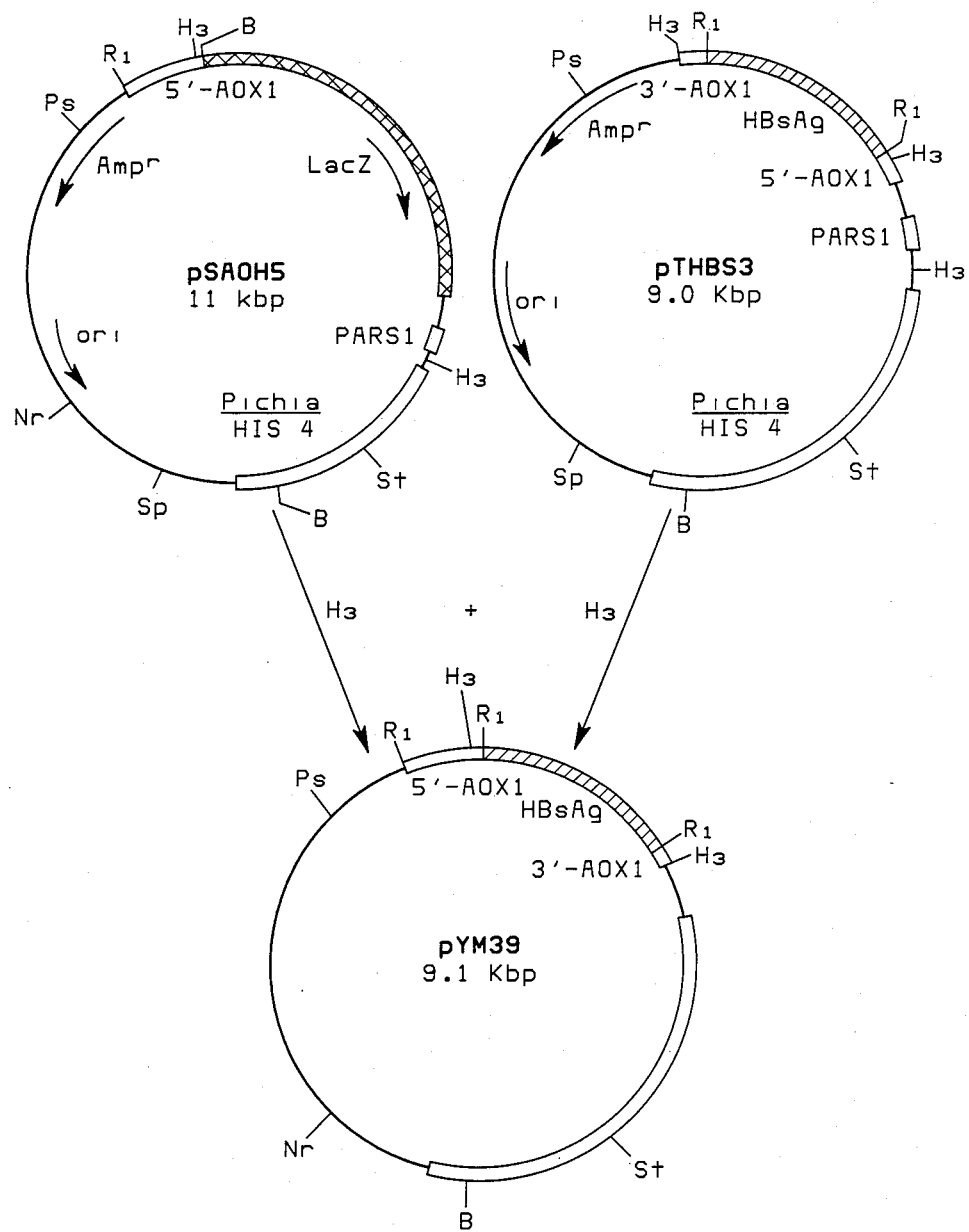
FIG. 9 illustrates the construction of plasmid pYM39 from plasmids pSAOH5 and pTHBS3.
Figure 10:
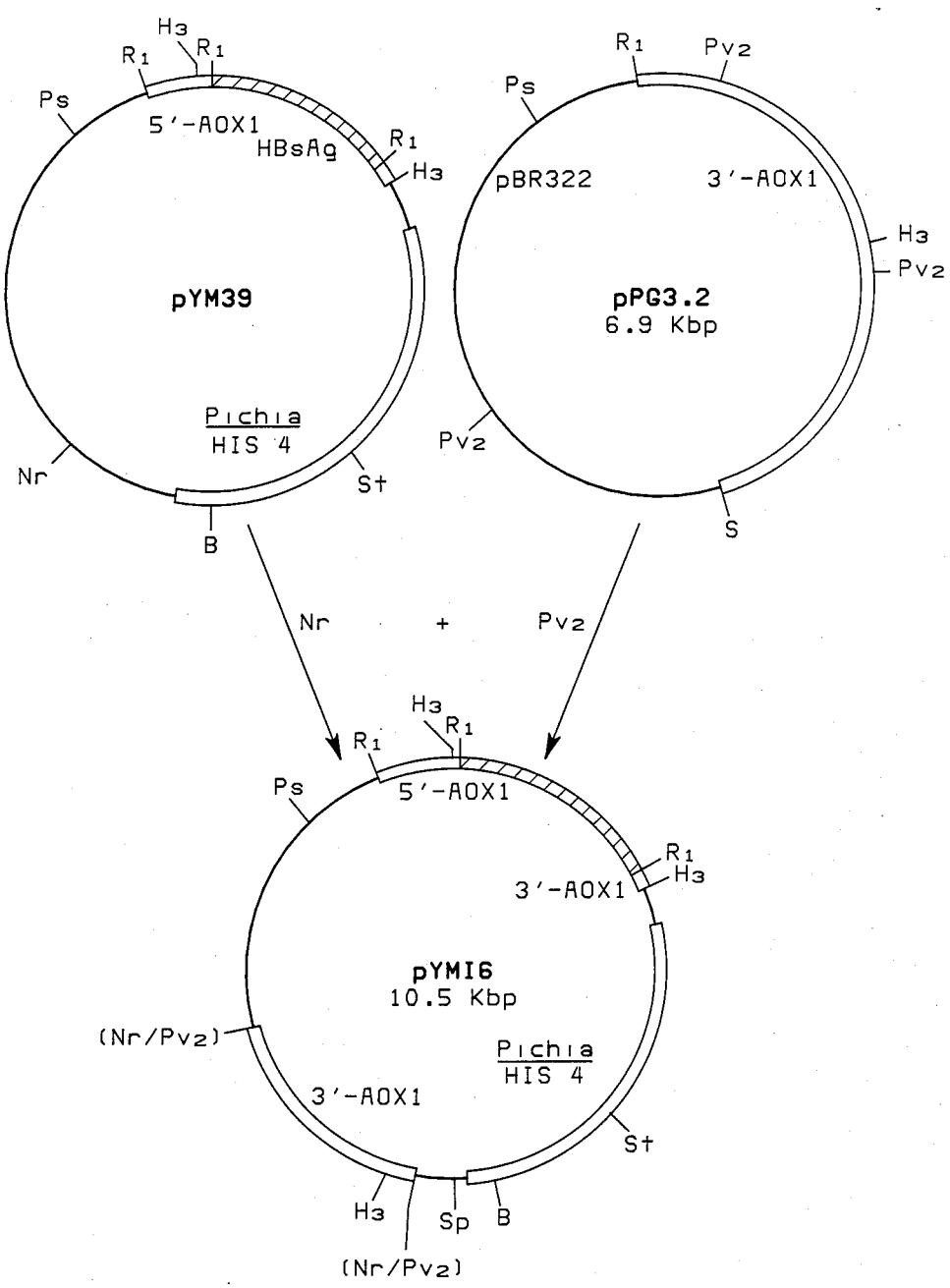
FIG. 10 illustrates the construction of plasmid pYMI6 from plasmids pYM39 and pPG3.2.
Figure 11:
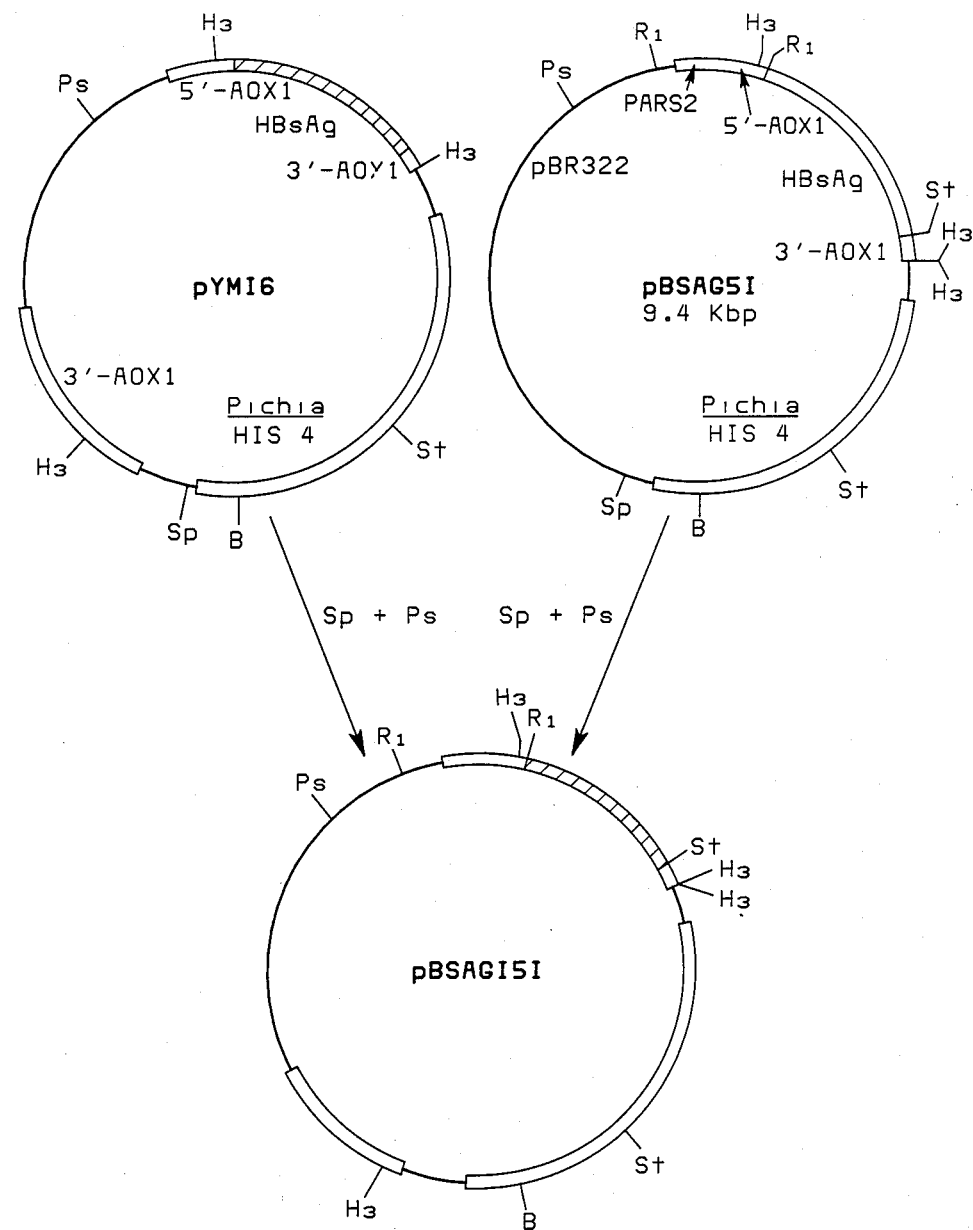
FIG. 11 illustrates the construction of plasmid pBSAGI5I from plasmid pYMI6 and pBSAG5I.
Figure 12:
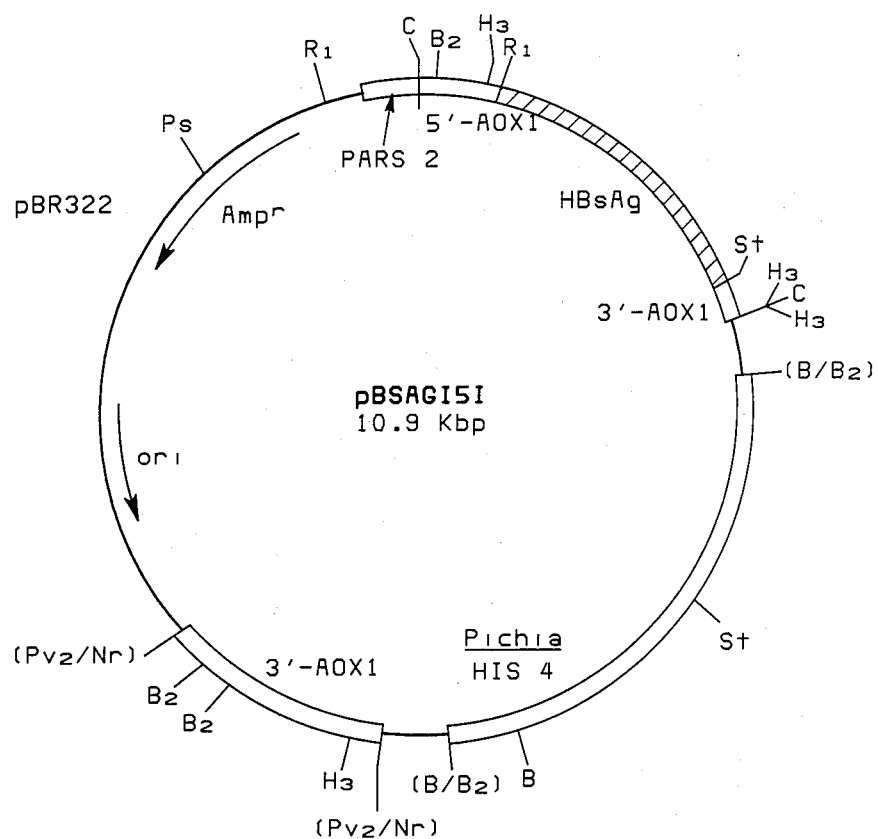
FIG. 12 is a restriction map showing greater detail of plasmid pBSAGI5I than set forth in FIG. 11.

In this example of site-directed insertion/deletion, the entire coding sequence of the AOX1 gene was deleted and the Hepatitis B surface antigen (HBsAg) gene was inserted under control of the AOX1 gene promoter which remains in the genome. For this P. pastoris host construction, plasmid pBSAGI5I was created (deposited in an E. coli host with the Northern Regional Research Center of the United States Department of Agriculture, in Peoria, Ill., and available to the public without restriction upon issuance of a patent from this application, with accession number NRRL B-18021; FIG. 12). The plasmid contains a 1.0 kbp fragment from sequences flanking the 5'-terminus of the AOX1 gene followed by the hepatitis B surface antigen (HBsAg) sequence and the 300 bp AOX1 terminator fragment, all assembled as shown in FIGS. 9, 10 and 11. The expression cassette was followed by the 2.7 kbp fragment encoding the Pichia HIS4 gene and finally, a 1.5 kbp PvuII fragment containing sequences 3' to the AOX1 gene. When pBSAGI5I was digested with BglII, a 7.2 kbp linear vector was released which contained 0.85 lbp of 5'-AOX1 gene sequence at one terminus and 1.1 kbp of 3'-AOX1 sequence at the other terminus. BglII-cut pBSAGI5I was transformed into CS115 by selecting for histidine prototrophy, transformants were extracted from the regeneration agar and sonicated as described in Example II, and spread on SD medium agar plates with 0.1% glucose (instead of 2.0%). The colonies which resulted were then replica plated onto minimal agar plates with the following carbon sources: (1) no carbon source, (2) 0.5% methanol, and (3) 2% glucose. On the average 32% of the colonies examined could not grow normally on methanol.

Figure 13:
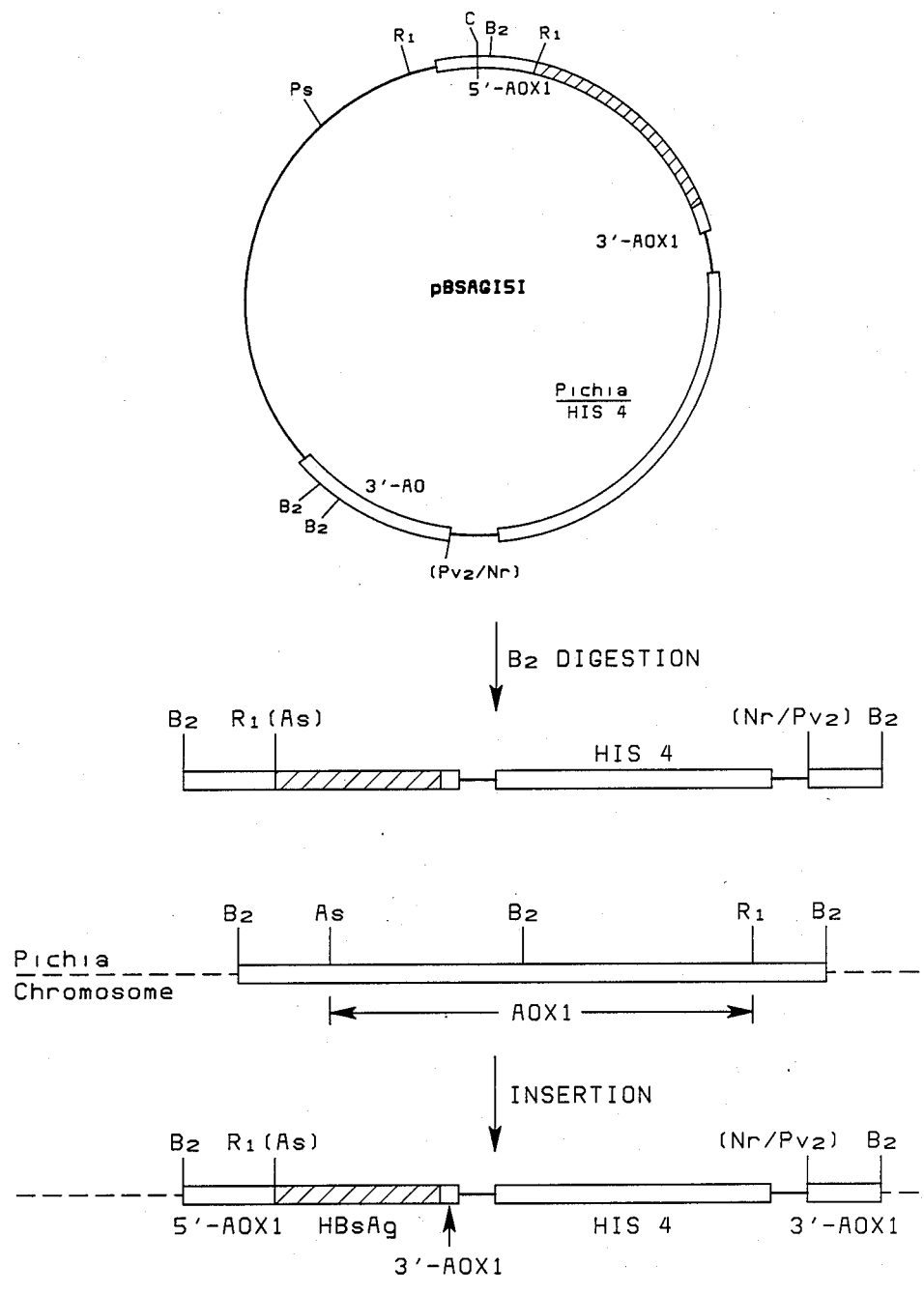
FIG. 13 illustrates the insertion of a portion of plasmid pBSAGI5I into the alcohol oxidase locus of the Pichia chromosome.

Southern blot analysis of the genomic DNAs from two of the methanol nonutilizers demonstrated that the AOX1 gene was deleted and that the vector sequences were inserted as shown in FIG. 13.

When grown in methanol, the GS115-pBSAFI5I strain (aox1::HBsAg-HIS4) expressed HBsAg in higher levels than expressed by fully alcohol oxidase competent cells similarly transformed.

EXAMPLE VII

Idenficiation of the Second Alcohol Oxidase Gene of P. pastoris by the Site-Directed Insertion Technique The presence of a second alcohol oxidase gene can be inferred from the following observations: (1) Southern blots in which probes from either AOX cDNA or a genomic DNA were hybridized to restricted Pichia genomic DNAs always showed at least two bands; (2) two Pichia genomic DNA fragments were originally isolated which were similar but not identical to each other (see FIG. 16); and (3) mutant Pichia strains such as KM71 and GS115-pBSAGI5I in which the primary AOX gene (AOX1), was deleted or disrupted could still grow on methanol and contained alcohol oxidase activity. The growth rate and AOX activity in methanol-growth cells of these Aox⁻ strains was much less then in isogenic-Aox1+ strains. Therefore, it appears that the second AOX gene (AOX2) is expressed at a lower level or that its product is less active on methanol. In Example IV, it was demonstrated that the Pichia DNA fragment in pPG4.0 contains the AOX1 gene.

Figure 14:
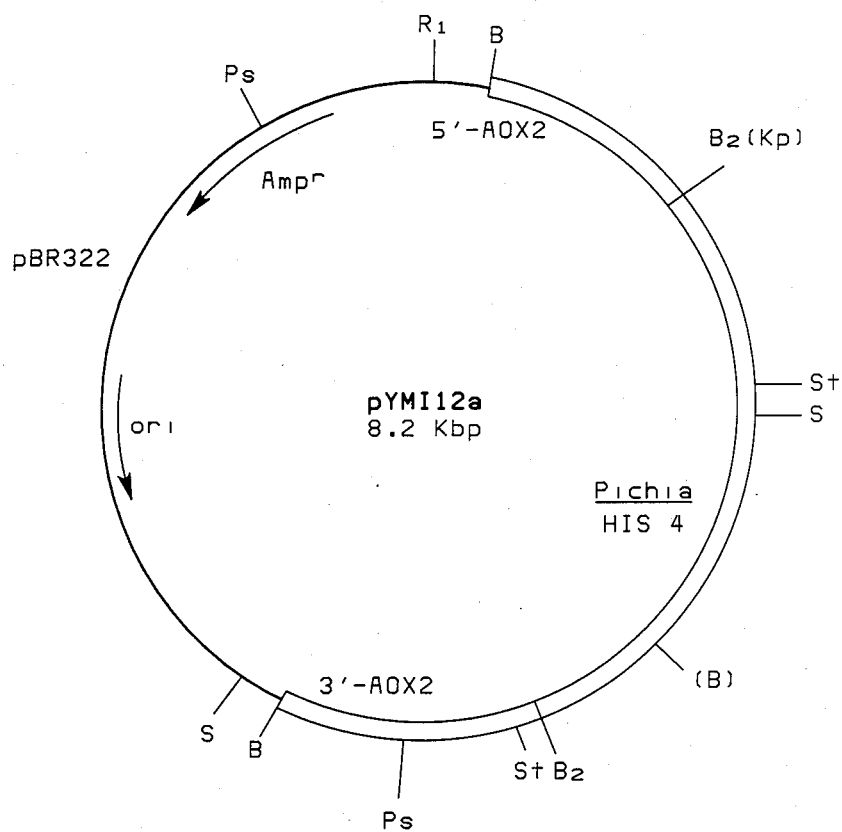

The most convincing method of demonstrating that the genomic DNA fragment from pPG3.0 contains at least a portion of the AOX2 gene is by constructing a mutant strain in which this putative AOX2 gene has been disrupted or deleted. For this, the site-directed vector pYM112a was constructed (FIG. 14). The plasmid consists primarily of pPG3.0 (FIG. 16b) which contains the putative AOX2 gene on a 3.0 kbp BamHI fragment. A 2.7 kbp BglII fragment which contains the Pichia HIS4 gene was isolated from pYJ8 (FIG. 3; NRRL B-15889) and inserted in place of the sequences which were located between the BglII and left-most KpnI sites of pPG3.0. (The KpnI site was converted to a BglII site with an oligonucleotide adaptor prior to insertion; and the BamHI site of the HIS4 gene was destroyed by "filling in" prior to insertion in pPG3.0.) Comparison of the AOX1 and the putative AOX2 genes (FIG. 16) shows that this construction should result in the deletion of about 800 bp from the middle of AOX2. By digestion of pYMI12a with BamHI, a 4.5 kbp linear vector was released which contained the HIS4-gene fragment flanked by sequences from the putative AOX2 locus of 1.1 and 0.7 kbp, respectively (see FIG. 15).

This linear vector was transformed into the Aox1⁻ strain, KM71, (aox1 his4::SARG4), and transformants were isolated by selecting for histidine prototrophs. The transformants were then screened for the ability to utilize methanol by replica plating onto sets of agar plates.

The untransformed Aox1⁻ strain KM71 grew so slowly on methanol plates that if methanol was included in the agar, it evaporated before significant growth could be observed. This problem was solved by feeding methanol to the cells in vapor phase. For this procedure, about 0.2 mL of 100% methanol was placed under the lid of a plate which contained no carbon source in the agar medium. The plate was left at room temperature, and the lid was replaced every 2 to 4 days with a fresh methanol-containing lid. After about 1-2 weeks, the difference in methanol growth of wild type (Aox1+ Aox2+), and the mutant strains, (Aox1⁻ Aox2+) and (Aox1⁻ Aox2⁻) was clear.

Figure 15:
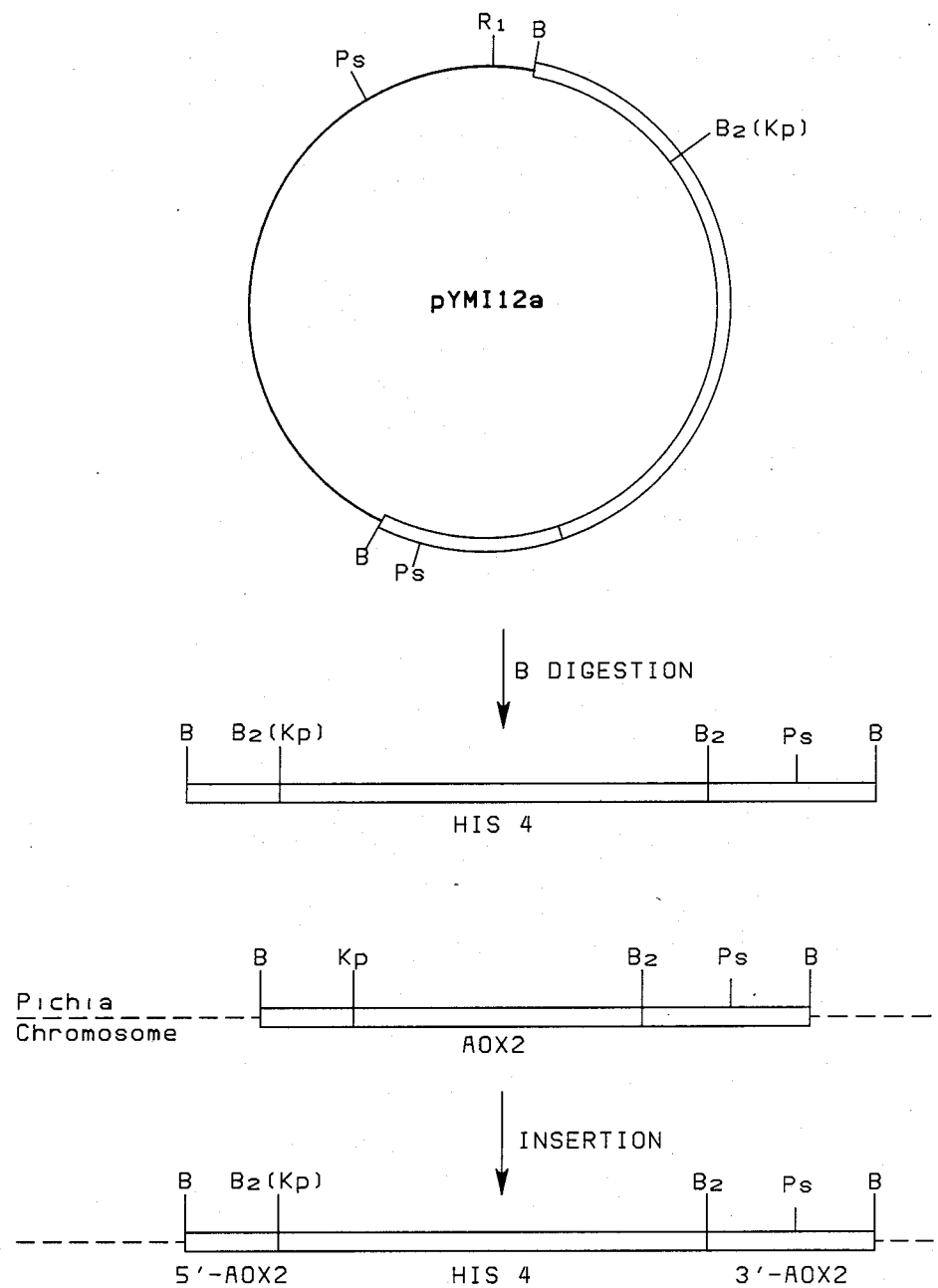
FIG. 15 illustrates the insertion of a portion of plasmid pYMI12a into the locus of the second Pichia alcohol oxidase gene (AOX2).

Following the vapor-phase feeding procedure, it was found that about 0.1% of His+ transformants from the Aox1⁻ strain were unable to grow on methanol. DNAs from eight of the Aox1⁻ Aox2⁻ His+ transformants were analyzed by the Southern filter hybridization procedure. Three of these DNAs contained the linear pYMI12a vector inserted as shown in FIG. 15. Analysis with one of the Aox1⁻ Aox2⁻ double mutants, KM7121 (NRRL Y-18019), showed that the strain absolutely does not grow on methanol and that the strain does not have detectable AOX activity. From these results with KM7121, it is clear that the Pichia fragment in pPG3.0 does contain sequences from a second AOX gene and that, other than these two alcohol oxidases, no other methanol-oxidizing activities exist in *P. pastoris*.

The examples have been provided merely to illustrate the practice of the invention and should not be read so as to limit the scope of the invention or the appended claims in any way. Reasonable variations and modifications, not departing from the essence and spirit of the invention, are comtemplated to be within the scope of patent protection desired and sought.

I claim:

1. A process for the site selected genomic modification of *Pichia pastoris* at a predetermined genomic site which comprises transforming a host strain of *Pichia pastoris* with a serially arranged linear DNA fragment comprising a first insertable DNA fragment,
a selectable marker gene, and
a second insertable DNA fragment;
wherein said first and second insertable DNA fragments are each at least about 200 nucleotides in length and have nucleotide sequences which are homologous with separate portions of the native *Pichia pastoris* genomic site at which genomic modification is to occur; wherein said first and second insertable DNA fragments are oriented with respect to one another in said linear DNA fragment as they are so oriented in the genomic with *Pichia pastoris;* wherein said marker gene is positioned between the first DNA insertable fragment and the second insertable DNA fragment and wherein said first and second insertable DNA fragments are selected from the group consisting of fragments of: the alcohol oxidase genes, and
the histidinol dehydrogenase gene.

2. A process in accordance with claim 1 wherein said linear DNA fragment further comprises a heterologous gene, wherein said heterologous gene, as well as said selectable marker gene, is positioned between the first insertable DNA fragment and the second insertable DNA fragment.

3. A process in accordance with claim 1 wherein said linear DNA fragment further comprises a regulatory region, and
a heterologous gene; wherein said heterologous gene is under the control of the regulatory region; and wherein the regulatory region-heterologous gene construct, in addition to said selectable marker gene, is positioned between the first insertable DNA fragment and the second insertable DNA fragment.

4. A process in accordance with claim 1 wherein said first and second insertable DNA fragments are fragments of the alcohol oxidase gene.

5. A process in accordance with claim 4 wherein said first and second insertable DNA fragments are fragments of the AOX1 gene.

6. A process in accordance with claim 4 wherein said first and second insertable DNA fragments are fragments of the AOX2 gene.

7. A process in accordance with claim 1 wherein said first and second insertable DNA fragments are fragments of the histidinol dehydrogenase gene.

8. An isolated serially arranged linear DNA fragment which comprises a first insertable DNA fragment, a selectable marker gene, and a second insertable DNA fragment; wherein said first and second insertable DNA fragments are each at least 200 nucleotides in length and have nucleotide sequences which are homologous with portions of the genomic DNA of *Pichia pastoris;* wherein said first and second insertable DNA fragments are oriented with respect to one another in said linear DNA fragment as they are so oriented in the genome of *Pichia pastoris;* wherein said marker gene is positioned between the first insertable DNA fragment, the second insertable DNA fragment, and wherein said first and second insertable DNA fragments are selected from the group consisting of fragments of:

the alcohol oxidase genes, and the histidinol dehydrogenase gene.

9. A linear DNA fragment in accordance with claim 8 wherein said linear DNA fragment further comprises:

a heterologous gene, wherein said heterologous gene, as well as said selectable marker gene is positioned between the first insertable DNA fragment and the second insertable DNA fragment.

10. A DNA fragment in accordance with claim 9 wherein said linear DNA fragment further comprises a resulatory region, and a heterologous gene; wherein said heterologous gene is under the control of the regulatory region; and wherein the regulatory region-heterologous gene construct, in addition to said selectable marker gene, is positioned between the first insertable DNA fragment and the second insertable DNA fragment.

11. A DNA fragment in accordance with claim 8 wherein said first and second insertable DNA fragments are fragments of the alcohol oxidase gene.

12. A DNA fragment in accordance with claim 11 wherein said first and second insertable DNA fragments are fragments of the AOX1 gene.

13. A DNA fragment in accordance with claim 11 wherein said first and second insertable DNA fragments are fragments of the AOX2 gene.

14. A DNA fragment in accordance with claim 8 wherein said first and second insertable DNA fragments are fragments of the histidinol dehydrogenase gene.

15. A linear DNA fragment in accordance with claim 8 wherein said DNA fragment further comprises bacterial plasmid DNA.

16. A closed circular plasmid comprising the linear DNA portion of claim 8, and bacterial plasmid DNA; wherein said bacterical plasmid DNA is positioned between the first insertable DNA fragment and the second insertable DNA fragment.

* * * * *